(12) United States Patent
Ketner et al.

(10) Patent No.: US 7,022,496 B2
(45) Date of Patent: Apr. 4, 2006

(54) USE OF GENE PRODUCT OF ADENOVIRUS EARLY REGION 4 ORF-6 TO INHIBIT REPAIR OF DOUBLE-STRAND BREAKS IN DNA

(75) Inventors: Gary Ketner, Columbia, MD (US); Julie L. Boyer, New York, NY (US)

(73) Assignee: The Johns Hopkins University, Baltimore, MD (US)

( * ) Notice: Subject to any disclaimer, the term of this patent is extended or adjusted under 35 U.S.C. 154(b) by 513 days.

(21) Appl. No.: 09/904,698

(22) Filed: Jul. 13, 2001

(65) Prior Publication Data

US 2002/0193328 A1 Dec. 19, 2002

Related U.S. Application Data

(60) Provisional application No. 60/218,498, filed on Jul. 14, 2000.

(51) Int. Cl.
*C12P 21/00* (2006.01)

(52) U.S. Cl. ............... 435/69.1; 424/184.1; 424/233.1; 424/204.1; 424/277.1; 424/278.1; 530/300; 530/350; 530/23.72

(58) Field of Classification Search ............ 424/184.1, 424/233.1, 204.1, 277.1, 278.1; 530/350, 530/300; 536/23.72
See application file for complete search history.

(56) References Cited

OTHER PUBLICATIONS

Ramalingam et al., Blood May 1999, vol. 93, pp. 2936-2944.*
Vollmer et al., Cancer Res. 1999 vol. 59, pp. 4369-4374.*
Boyer,et al., Adenovirus E4 34K and E4 11k Inhibit Double Strand Break Repair and Are Physically Associated with the Cellula DNA-Dependent Protein Kinase, Virology, vol. 263, Issue 2, Oct. 25, 1999, pp. 307-312.*
Expression of the DNA-PK binding protein E4-34K fails to confer radiation sensitivity to mammallan cells; S. J. Collins, et al.; International Journal of Radiation Biology 2003, vol. 79, No. 1, 53-60 Taylor and Francis Healthsciences.

* cited by examiner

*Primary Examiner*—James Housel
*Assistant Examiner*—Myron G. Hill
(74) *Attorney, Agent, or Firm*—Whitman, Curtis & Christofferson, PC

(57) ABSTRACT

The present invention provides a modified adenovirus comprising genomic adenoviral DNA which has been modified so that (i) the only gene product of the early region (E4) that is expressed is open reading frame 6 (ORF-6), (ii) neither the gene product of the E1A region nor the gene product of the E1B region is expressed, and (iii) no other early or late gene products are expressed. The present invention also provides methods of inhibiting repair of breaks in double-stranded DNA in a cell, preventing concatamerization of linear wild-type adenoviral DNA, inhibiting V(D)J recombination of nucleic acid sequences encoding immunoglobulins, preventing apoptosis, and preventing and treating cancer.

4 Claims, 21 Drawing Sheets

SEQUENCE LISTING

<160> NUMBER OF SEQ ID NOS: 2

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucloetide primer

<400> SEQUENCE: 1
cccaccctaa cagagatgac c                     21

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide pirmer

<400> SEQUENCE: 2
gcggccgcaa ttcccgggg                        19

USE OF GENE PRODUCT OF ADENOVIRUS EARLY REGION 4 ORF-6 TO INHIBIT REPAIR OF DOUBLE-STRAND BREAKS IN DNA

This application claims the benefit of U.S. Provisional Application No. 60/218,498, filed Jul. 14, 2000, the content of which is hereby incorporated by reference.

The invention disclosed herein was made with Government support under Grant Nos. R01 GM31452 and CA26239 from the National Institutes of Health. Accordingly, the U.S. Government has certain rights in this invention.

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to more fully describe the state of the art to which this invention pertains.

The widespread interest in the potential of adenoviruses as therapeutic vectors has overshadowed the utility of hybrid viruses as tools to study intracellular processes. The origins of such research began with the analysis of human adenovirus-SV40 hybrids that were capable of replication in otherwise nonpermissive monkey cells because of the expression of a domain of the SV40 T antigen [reviewed in Klessig (1984)], but the full potential of this approach was realized only when it became practicable to create the desired recombinant genomes in vitro [for early reviews see Gluzman et al. (1982) and Berkner (1988)]. Although adenovirus vectors expressing a wide variety of individual gene products have been produced, very few have been created to investigate the mechanisms underlying DNA repair or recombination. The exceptions include those that express the cre site-specific recombinase, which has been used to restructure viral and cellular genomes in vivo (Anton and Graham, 1995; Wang et al., 1995; Parks et al., 1996; Hardy et al., 1997; Kanegae et al., 1995; Wang et al., 1996), and the bacteriophage T4 endonuclease denV, which was shown to be capable of functioning as a replacement for the mutant protein in xeroderma pigmentosum cells of groups A, C, and E (Colicos et al., 1991). These experimental precedents suggest that adenovirus vectors hold great promise as tools to investigate DNA metabolism. They can be used to infect a wide range of cell lines from a variety of species, including cells with deficiencies in DNA repair.

Among the processes that might be investigated using adenovirus vectors are those involved in double-strand break (DSE) repair (DSBR) in mammalian cells. The mechanisms by which mammalian cells repair DNA double-strand breaks (DSBs) are not fully understood at the molecular level. The nuclear-replicating DNA-containing viruses are not only subject to these repair mechanisms, but can also be used to investigate them. One way to exploit the virus systems is to construct vectors that express endonucleases that create DSBs in specific targets and then to follow DSB repair under a variety of experimental conditions. Double-strand breaks arise in cellular DNA as the result of the action of DNA-damaging agents and of normal cellular processes such as immunoglobulin gene rearrangement. Double-strand breaks interfere with cellular DNA replication and chromosome segregation and are lethal if unrepaired. Therefore, mammalian cells contain an efficient double-strand break repair (DSBR) system that rapidly joins free double-stranded ends by an homology-independent mechanism (Jeggo, 1998). The cellular DSBR system is active both on broken chromosomal DNA and on exogenous DNAs introduced into cells, and the linear adenovirus genome is a potential substrate for concatemerization or circularization by the DSBR system in infected cells. DSBR is not only crucial to the survival of the cell, but also is involved in the developmentally regulated rearrangement of B cell and T cell receptor loci [for a recent review see Lieber (1998)]. Genetic and biochemical data from both mammalian cells and fungi show that DSBR depends on the activities of a large set of proteins including DNA-dependent protein kinase (PK); DNA ligase IV and its stimulatory protein, the product of the XRCC4 gene; and the protein products of the Mre11, Rad50, and mammalian NBS or the yeast equivalent Xrs2 genes. Recently, an in vitro system for DSBR, which is dependent on this set of proteins (Baumann and West, 1998), was described. However, despite advances in identifying the components of DSBR in mammalian cells, many questions remain about the precise mechanisms operating on DSBs occurring in vivo, and there continues to be a need for simple assays for DSBR. Until recently, such assays have depended either on the transfection of restriction enzyme-cleaved substrate DNA [reviewed in Roth and Wilson (1988)] or on the introduction of purified restriction enzymes themselves into the cell [see for example Phillips and Morgan (1994); Liu and Bryant (1993); Costa and Bryant (1991)]. Subsequent analyses of the fates of the broken DNAs have usually taken place after a long period of time and/or the selection of specific recombinant products. Despite the success of these methods in suggesting several important aspects of DSBR in mammalian cells (Roth and Wilson, 1988), they do not allow the fate of DSBs created in vivo at specific genetic locations to be followed in real time. This approach has been particularly productive in *Saccharomyces cerevisiae*, in which the mating type switch HO endonuclease and its recognition site have been exploited to examine the mechanisms of both homologous and nonhomologous recombinational repair [reviewed in Haber (1995)]. Most recently, conditional expression of the EcoRI endonuclease has allowed detailed genetic analysis of those genes essential for nonhomologous DSBR in *S. cerevisiae* (Lewis et al., 1998, 1999). In mammalian cells, the development of cell lines and plasmid vectors expressing the intron-encoded enzyme I-SceI has allowed a closer look at the repair of specific DSBs, created and resolved in vivo (Rouet et al., 1994a,b; Sargent et al., 1997; Choulika et al., 1995). This system has been used, for example, to show that mutations in Ku80 abolish end-joining, while permitting normal levels of homologous recombination (Liang et al., 1996), to demonstrate loss of heterozygosity following the repair of an induced DSB (Moynahan and Jasin, 1997), to estimate the lengths of gene conversion tracts (Elliott et al., 1998), and to examine the control of translocation (Richardson et al., 1998). This in vivo approach is more likely to give a true picture of the physiological consequences of the formation and processing of DSBs.

Adenovirus vectors expressing the yeast mating-type switching endonuclease HO may be used to examine the formation and fate of double-strand breaks created in adenovirus genomes containing an HO recognition site. The results show that the HO recognition site can be cleaved by the HO gene product in mammalian cells, but that in permissive infections repair is below the limits of detection of the methods employed. Broken genome fragments accumulate and those containing packaging signals can be encapsidated. However, in nonpermissive infections in which E4 product expression is absent or severely reduced, endjoining of fragments takes place, suggesting that one or more E4 products inhibit DSBR.

The cellular DSBR system is active both on broken chromosomal DNA and on exogenous DNAs introduced into cells, and the linear adenovirus genome is a potential substrate for concatemerization or circularization by the DSBR system in infected cells. However, in wild-type adenovirus infections intracellular adenovirus DNA, with the exception of branched replication intermediates, is almost exclusively monomeric and linear. Weiden and Ginsberg (1994) reported that adenovirus mutants lacking early region 4 (E4) produced concatemers of viral DNA in infected Hela cells, and that the presence of either E4 ORF6, which encodes a 34 kDa protein (E4 34k), or E4 ORF3, which encodes an 11 kDa protein (E4 11k), suppressed concatemer formation. End-to-end joining by the DSBR system was suggested as a mechanism for concatemer formation. If concatemers arise in that way, the E4 proteins might prevent concatemerization by antagonizing DSBR in infected cells. As disclosed herein, that hypothesis was investigated by examining concatemer formation in cells that lack the cellular DNA-dependent protein kinase (DNA PK), an essential element of the DSBR system (Jeggo, Taccioli, and Jackson, 1995), by assessing the effects of E4 products on DSBR-dependent V(D)J recombination, by assessing the effects of E4 products on DSBR-dependent V(D)J recombination, and by examining the effects of E4 products on repair by the DSBR system of double-strand breaks in the viral genome induced by a site-specific endonuclease, the yeast mating type switching endonuclease (HO) endonuclease.

SUMMARY OF THE INVENTION

The present invention provides a modified adenovirus comprising genomic adenoviral DNA which has been modified so that (i) the only gene product of the early region (E4) that is expressed is open reading frame 6 (ORF-6), (ii) neither the gene product of the E1A region nor the gene product of the E1B region is expressed, and (iii) no other early or late gene products are expressed.

The present invention provides a method of inhibiting repair of breaks in double-stranded DNA in a cell which comprises introducing into the cell a modified adenovirus comprising genomic adenoviral DNA which has been modified so that (i) the only gene product of the early region (E4) that is expressed is open reading frame 6 (ORF-6) and (ii) neither the gene product of the E1A region nor the gene product of the E1B region is expressed, and (iii) no other early or late gene products are expressed.

The present invention provides a method of preventing cancer in a subject which comprises introducing into a cell of the subject a modified adenovirus comprising genomic adenoviral DNA which has been modified so that (i) the only gene product of the early region (E4) that is expressed is open reading frame 6 (ORF-6) and (ii) neither the gene product of the E1A region nor the gene product of the E1B region is expressed, and (iii) no other early or late gene products are expressed.

The present invention provides a method of treating cancer in a subject which comprises introducing into a cancer cell of the subject a modified adenovirus comprising genomic adenoviral DNA which has been modified so that (i) the only gene product of the early region (E4) that is expressed is open reading frame 6 (ORF-6) and (ii) neither the gene product of the E1A region nor the gene product of the E1B region is expressed, and (iii) no other early or late gene products are expressed.

The present invention provides a method of preventing concatamerization of a linear wild-type adenoviral DNA which comprises introducing into a cell comprising the wild-type adenoviral DNA, a modified adenovirus comprising genomic adenoviral DNA which has been modified so that (i) the only gene product of the early region (E4) that is expressed is open reading frame 6 (ORF-6) and (ii) neither the gene product of the E1A region nor the gene product of the E1B region is expressed, and (iii) no other early or late gene products are expressed.

The present invention provides a method of inhibiting V(D)J recombination of nucleic acid sequences encoding immunoglobulins in a cell of the immune system which comprises introducing into the cell, a modified adenovirus comprising genomic adenoviral DNA which has been modified so that (i) the only gene product of the early region (E4) that is expressed is open reading frame 6 (ORF-6) and (ii) neither the gene product of the E1A region nor the gene product of the E1B region is expressed, and (iii) no other early or late gene products are expressed.

The present invention provides a method of preventing in a cell apoptosis induced by viral DNA replication in the cell which comprises introducing into the cell, a modified adenovirus comprising genomic adenoviral DNA which has been modified so that (i) the only gene product of the early region (E4) that is expressed is open reading frame 6 (ORF-6) and (ii) neither the gene product of the E1A region nor the gene product of the E1B region is expressed, and (iii) no other early or late gene products are expressed.

The present invention provides a method of increasing efficiency of a chemotherapeutic agent for treating cancer in a subject which comprises: a) introducing into cancer cells of the subject a modified adenovirus comprising genomic adenoviral DNA which has been modified so that (i) the only gene product of the early region (E4) that is expressed is open reading frame 6 (ORF-6) and (ii) neither the gene product of the E1A region nor the gene product of the E1B region is expressed, and (iii) no other early or late gene products are expressed and b) administering the chemotherapeutic agent to the subject.

The present invention provides a method of inhibiting repair of breaks in double-stranded DNA in a cell which comprises introducing into the cell the gene product of the early region 4 (E4) open reading frame 6 (ORF-6) of genomic adenoviral DNA.

The present invention provides a method of preventing cancer in a subject which comprises introducing into a cell of the subject the gene product of the early region 4 (E4) open reading frame 6 (ORF-6) of genomic adenoviral DNA.

The present invention provides a method of treating cancer in a subject which comprises introducing into a cancer cell of the subject the product of the early region 4 (E4) open reading frame 6 (ORF-6) of genomic adenoviral DNA.

The present invention provides a method of preventing concatamerization of a linear wild-type adenoviral DNA which comprises introducing into a cell comprising the wild-type adenoviral DNA, the product of the early region 4 (E4) open reading frame 6 (ORF-6) of genomic adenoviral DNA.

The present invention provides a method of inhibiting V(D)J recombination of nucleic acid seqeuences encoding immunoglobulins in a cell of the immune system which comprises introducing into the cell, the product of the early region 4 (E4) open reading frame 6 (ORF-6) of genomic adenoviral DNA.

The present invention provides a method of preventing in a cell apoptosis induced by viral DNA replication in the cell which comprises introducing into the cell, the product of the early region 4 (E4) open reading frame 6 (ORF-6) of genomic adenoviral DNA.

The present invention provides a method of increasing efficiency of a chemotherapeutic agent for treating cancer in a subject which comprises: a) introducing into cancer cells of the subject the product of the early region 4 (E4) open reading frame 6 (ORF-6) of genomic adenoviral DNA and b) administering the chemotherapeutic agent to the subject.

A. The HO gene sequence located in the E3 region in the plasmid pPF446::HO gene. The HO gene sequence replaces the XbaI to NotI fragment of plasmid pPF446, which contains adenovirus DNA from the BamHI site at bp 21,562 to the right-hand end at bp 35,935. Numbers in parenthesis represent Ad5 coordinates as described by Chroboczek et al. (1992). The predicted structure of the chimeric E3A transcript and mRNA is shown immediately below the plasmid, and the numbers in parentheses are calculated from the analysis of wild-type Ad5 E3 by Cladaras and Wold (1985).

B. Potential chimeric protein resulting from the insertion of the HO site sequence in the 11.6K gene. The 181-bp NotI fragment containing the HO site sequence was inserted at the unique NotI site in E3 in plasmid pPF446. The stop codon for the potential chimeric 11.6K/HO site sequence protein is the TAG to the left of the rightward NotI site.

C. The HO gene located in the E1 region. Plasmid pAdCMV::HO gene contains the ORF for the HO gene under the control of the CMV immediate-early promoter. Adenovirus numbering is according to Chroboczek et al. (1992), while numbers in parentheses refer to the plasmid sequence.

D. The location of the HO site in the E1A-deleted virus. The HO site sequence is inserted at a NotI linker located toward the left-hand end of the genome. The BstBI site is located in one of the expression cassettes present in this virus genome.

Figure 2A:
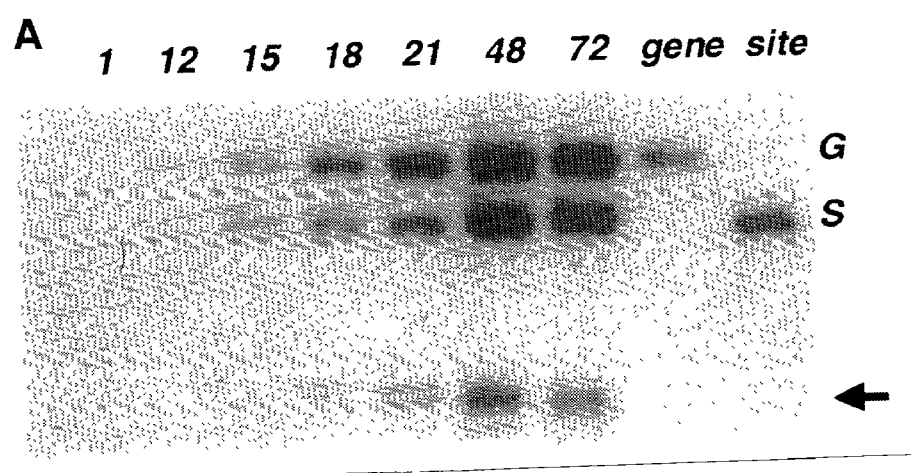
Figure 2B:
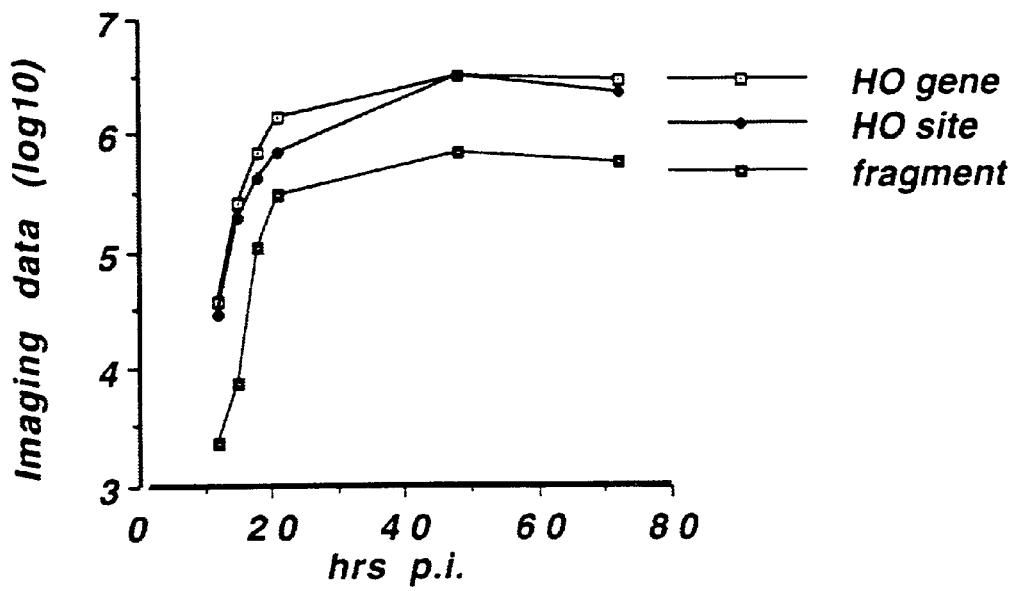
Figure 2C:
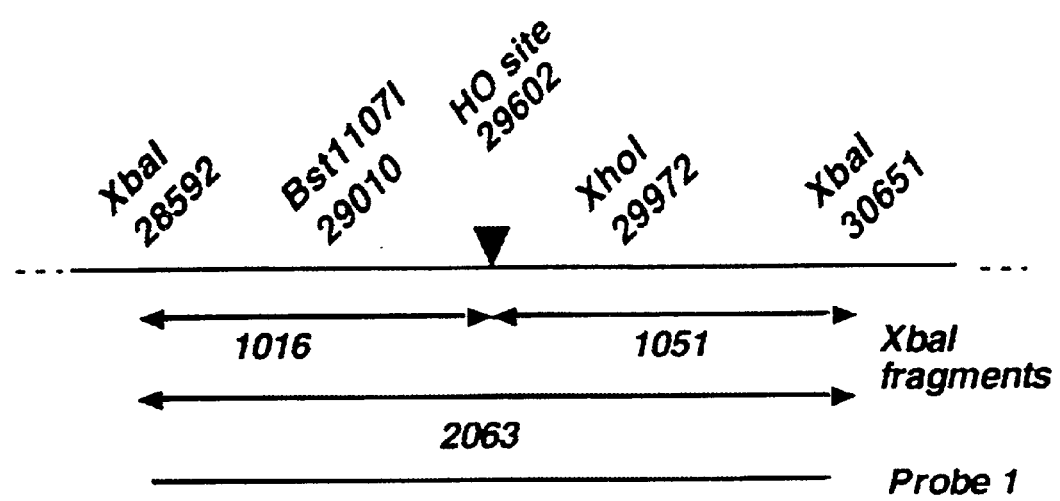

FIGS. 2A–2C Appearance and accumulation of cleaved fragments of viral DNA in A549 cells coinfected with E3::HO gene and E3::HO site viruses. A549 cells grown as monolayers in 35-mm dishes were infected at a m.o.i. of 10 of each virus, and intracellular DNA was isolated at the hours postinfection indicated above the lanes. DNA was digested with XbaI, and the fragments were separated by agarose gel eletrophoresis and analyzed by Southern transfer-hybridization, using radiolabeled probe 1 (see FIG. 4). The processed filter was quantitated using a PhosphorImager.

A. The image captured from the ImageQuant file. The DNAs from the single infections are shown in the last two lanes and are labeled "gene" and "site." The XbaI fragments from the HO gene and HO site virus genomes are labeled G and S, respectively, and the novel fragment of about 1 kb in size, present only in the coinfection, is indicated by the arrow.

B. Quantitation of the three species of DNA that accumulate during the infection.

C. Restriction enzyme map surrounding the E3::HO site. The fragments shown are thos expected to be produced by cleavage in vivo by HO endonuclease followed by XbaI digestion in vitro and the XbaI fragment uncleaved by HO endonuclease. Probe 1 (see legend to FIG. 4) will hybridize to all the fragments shown and one of 2817 nt in length derived from XbaI cleavage of DNA from the E3::HO gene. The sizes of fragments include any protruding 5' and 3' single strands and are given in nucleotides.

Figure 3:
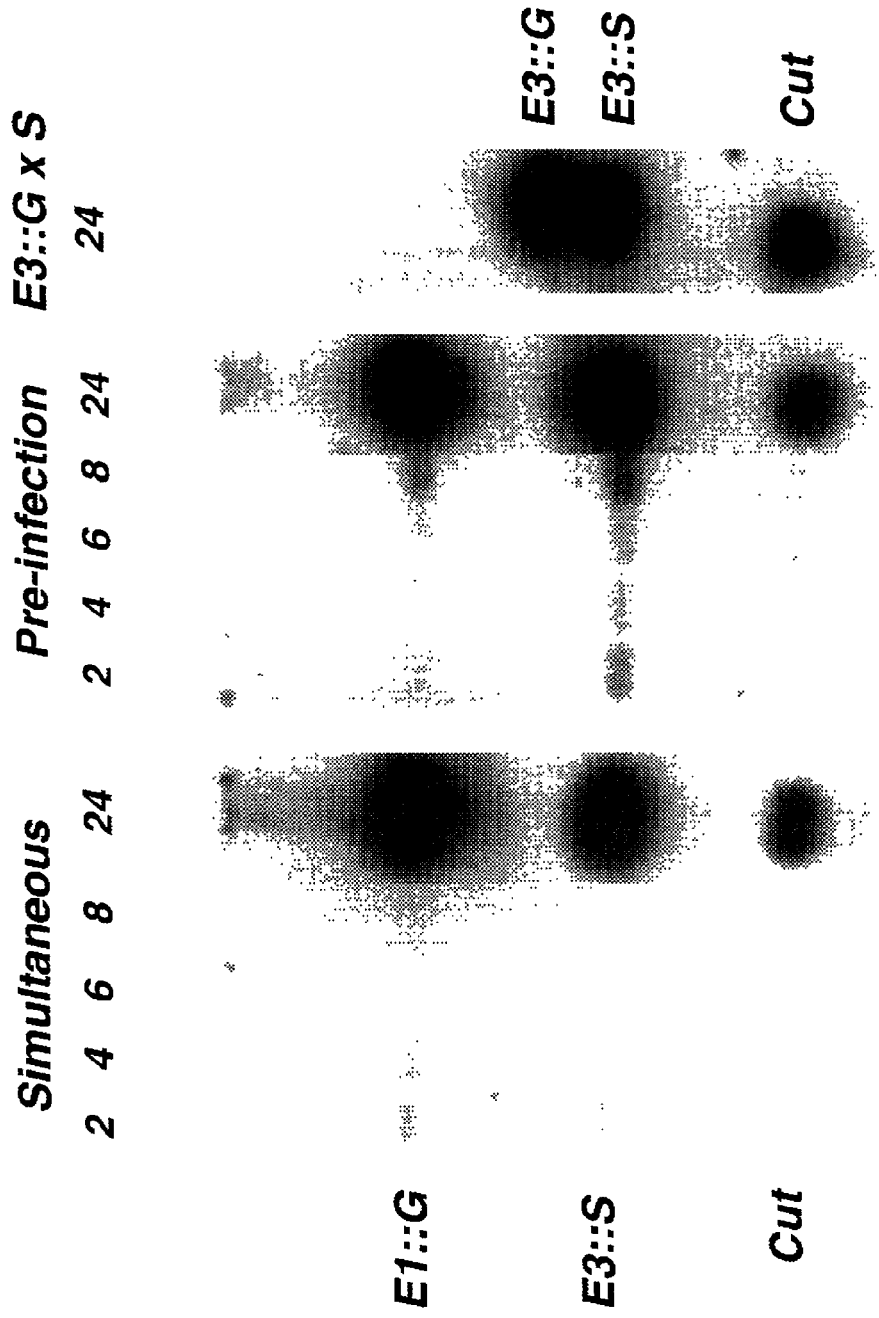

FIG. 3 Comparison of cleavage of E3::HO site sequences in coinfections of A549 cells with E3::HO site virus and E3::HO gene or E1::HO gene viruses. Monolayers of A549 cells in 35-mm dishes were infected with each virus at a m.o.i. of 10, and intracellular DNA was harvested at intervals and analyzed after digestion with XbaI, essentially as described in the legend to FIG. 2. Cells were infected with the two viruses simultaneously (simultaneous) or were infected with E1::HO gene virus 24 h prior to infection with E3::HO site virus (preinfection). The number above each lane in the autoradiogram refer to hours after infection with the E3::HO site virus. The right-hand panel shows DNA from a simultaneous infection with the E3::HO gene and site viruses, harvested at 24 h p.i. XbaI fragments labeled E1::G, E3::S, and E3::G refer to those derived from the E1::HO gene, E3::HO site, and E3::HO gene virus genomes, respectively. The novel band produced by HO endonuclease cleavage is labeled "Cut."

Figure 4A:
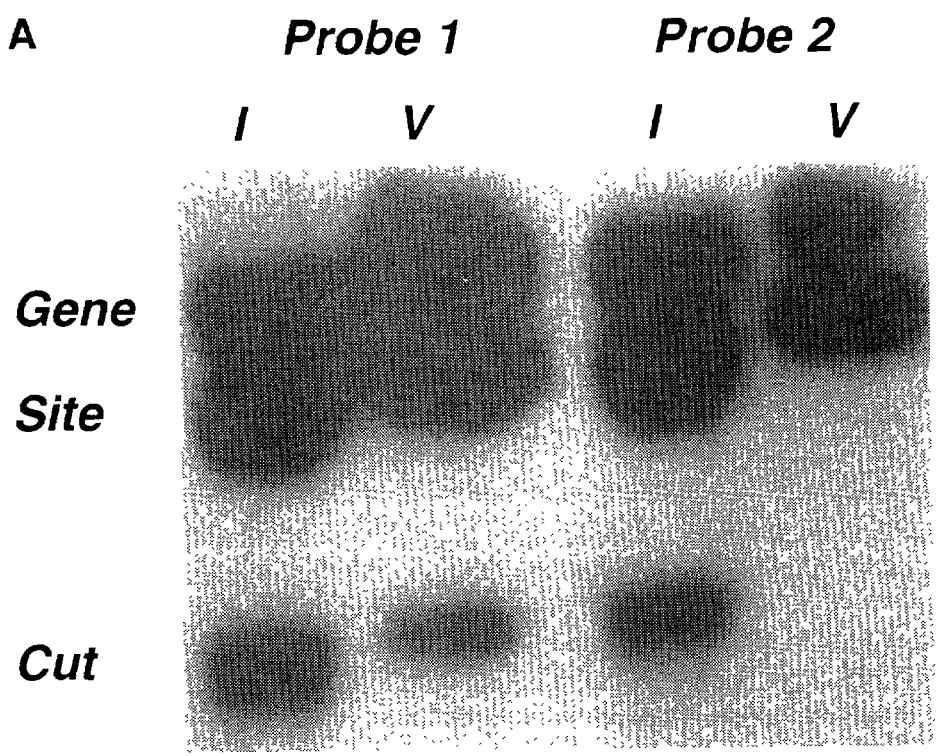
Figure 4B:
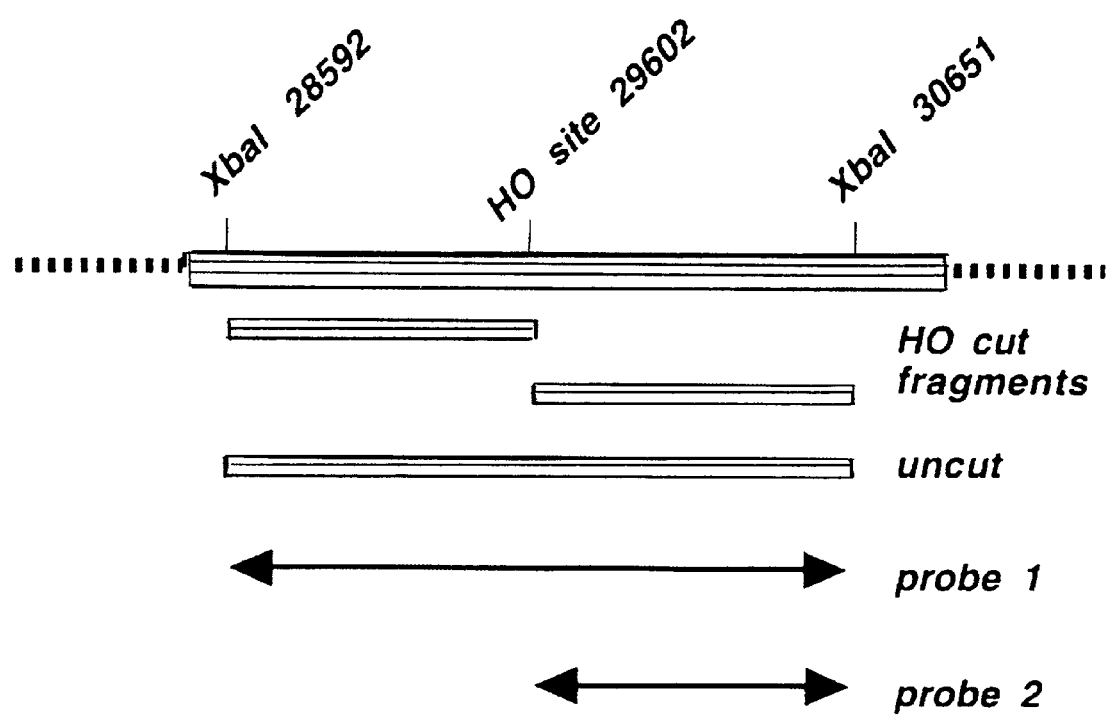

FIGS. 4A–4B Left-terminal genome fragments, created by HO endonuclease cleavage, can be found in complete virus particles, whereas right-terminal fragments are not.

A. A monolayer of A549 cells in a T 175-cm² flask was coinfected with E3::HO gene and E3::HO site viruses, each at a m.o.i. of 10, and viral DNA was isolated, either directly from a small sample of the infected cells or after purification of virus particles, from the remainder by CsCl density centrifugation. Analysis of the DNA was essentially as described in the legend to FIG. 2, but parallel filters were hybridized using probe 1, a plasmid containing the XbaI fragment encompassing the HO site, or probe 2, which is a derivative of probe 1 containing sequences to the right of the HO site. Lanes labeled I and V indicate DNA from intracellular and purified virus preparations, respectively. The positions of the XbaI fragments derived from HO gene and HO site virus genomes and the HO endonuclease-cleaved fragment are indicated (gene, site, and cut, respectively).

B. The positions of XbaI restriction sites flanking the HO endonuclease site and the expected XbaI fragments are indicated. Probe 1 is as described in the legend to FIG. 2, and probe 2 contains sequences from the XhoI site at nt 29,972 to the XbaI site at nt 30,651 of E3::HO site genome.

Figure 5A:
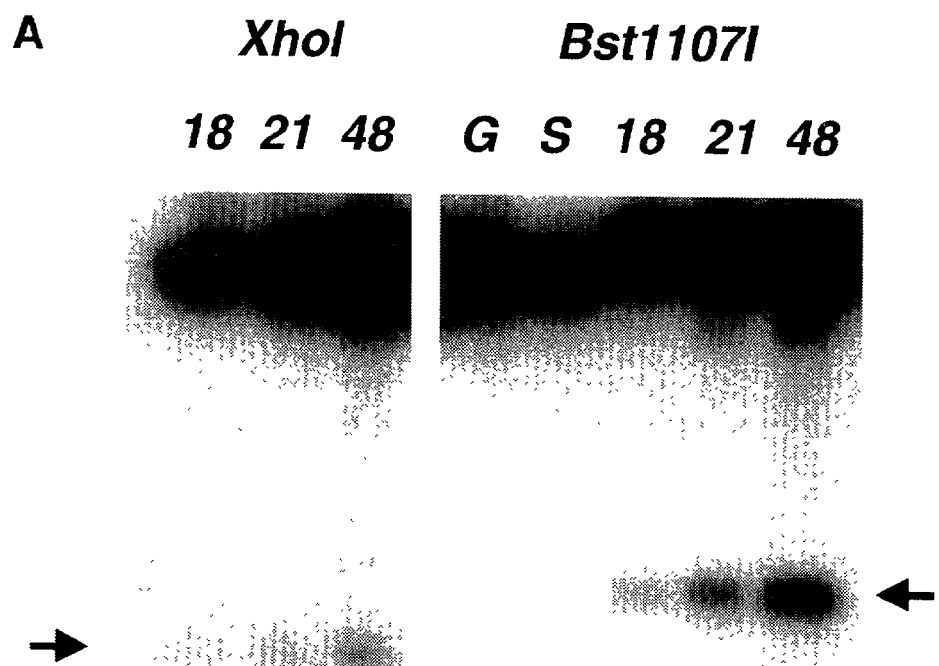
Figure 5B:
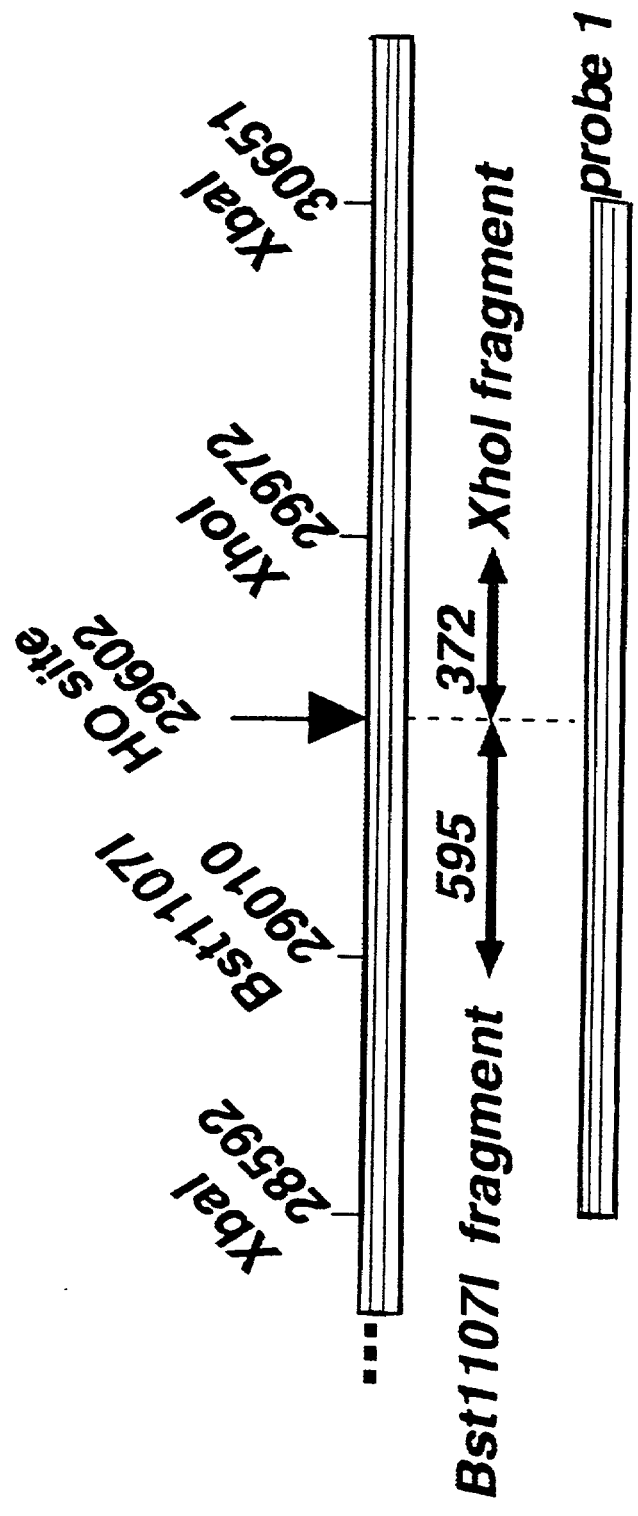

FIGS. 5A–5B Fragmented genomes, arising from coinfections of E3::HO gene and E3::HO site viruses, do not rejoin in trans to give head-to-head or tail-to-tail dimeric DNA species.

A. DNA samples from the infections described in the legend to FIG. 2 were digested with either Bst1107I or XhoI and analyzed by Southern hybridization, using probe 1. Hours postinfection are indicated above the lanes. G and S refer to DNAs isolated from single infections with the E3::HO gene and E3::HO site viruses, respectively, harvested at 48 h p.i. and digested with Bst11071. The image is derived from the ImageQuant file of the filter. The fragments of 595 and 372 nt in length produced by in vivo cleavage by HO endonuclease followed by in vitro digestion with Bst11071 and XhoI, respectively, are indicated by arrows (see B for origins of these small fragments). Large fragments at the top of the picture include species of 4812 nt and greaer, derived from digested E3::HO gene and E3::HO site virus genomes.

B. Positions of the restriction sites for the enzymes used in the analysis and the extent of probe 1 are indicated.

Figure 6A:
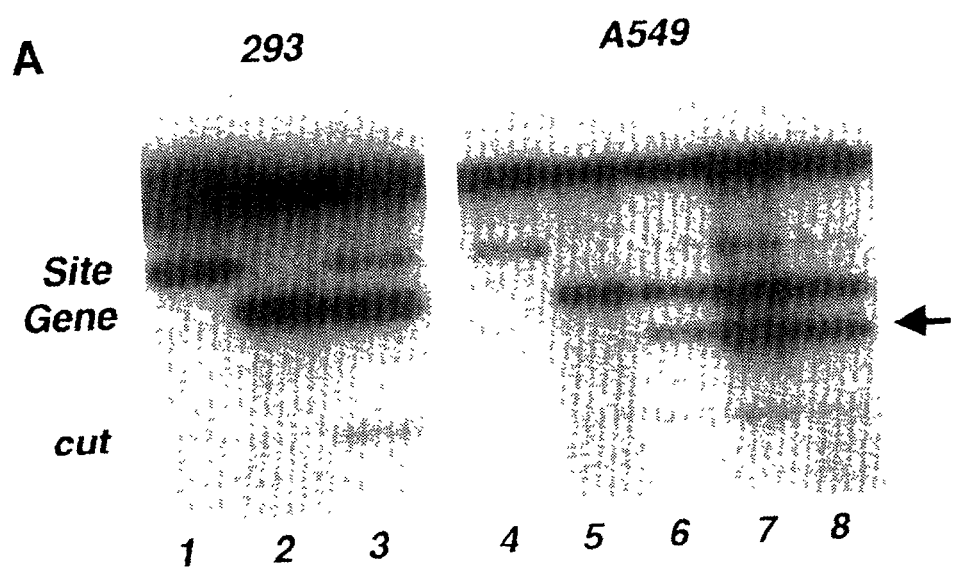
Figure 6B:
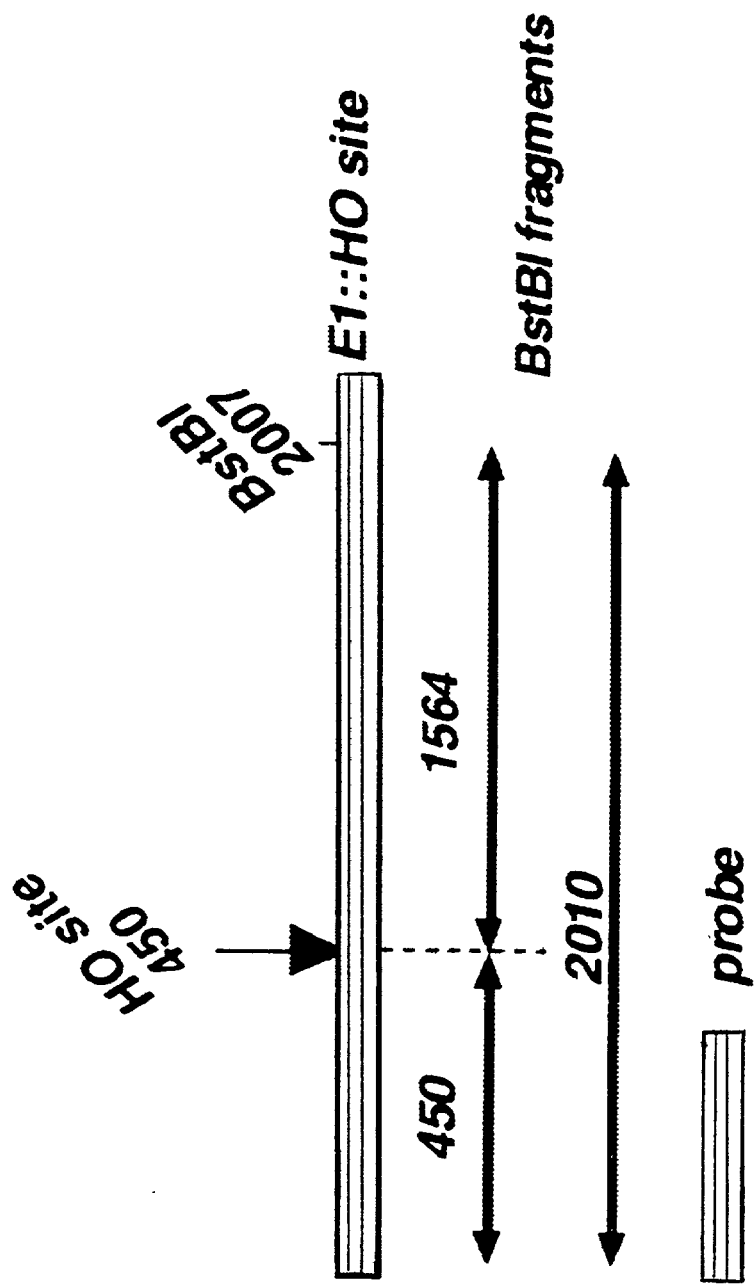

FIGS. 6A–6B Fragmented genomes, arising from coinfections of E1::HO gene and E1::HO site viruses, can form dimeric species in nonpermissive A549 cells but not in permissive 293 cells.

A. Cells in monolayer culture were infected with each virus at a m.o.i. of 10; intracellular DNA was isolated and digested with BstBI, before electrophoresis and Southern analysis, using a probe that recognizes the left-hand 355 bp of the adenovirus genome. The smaller BstBI DNA fragment DNA from the E1::HO gene virus genome, hubridizing to this probe, is 1278 nt long and is indicated ("gene"), while the fragment from the E1::HO site genome ("site") is 2010 nt long. If cleaved in vivo by the endonuclease, this fragment is reduced in size to 450 nt ("cut"). The fragment of 1564 nt to the right of the HO site is not recognized by the probe. The arrow on the right indicates the novel fragment of ~900 bp found only in the A549 cell samples. Lanes 1 and 4, infection with E1::HO site only; lanes 2 and 5, infection with E1::HO gene only; lanes 3 and 6, coinfections harvested 2 days p.i; lanes 7 and 8, coinfections harvested 4 and 8 days p.i.

B. Diagram of the locations of the fragments produced by cleavage by HO endonuclease in vivo and BstBI in vitro. The probe will also recognize fragments of ~35 kbp distal to the BstBI site derived from both E1::HO gene and E1::HO site virus genomes.

Figure 7A:
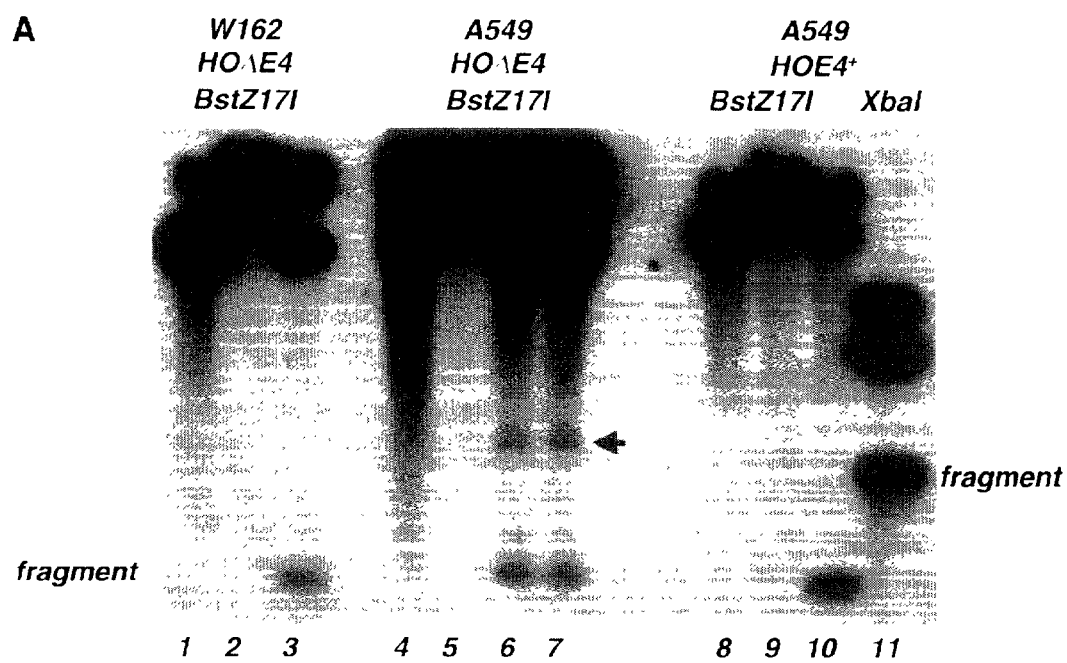
Figure 7B:
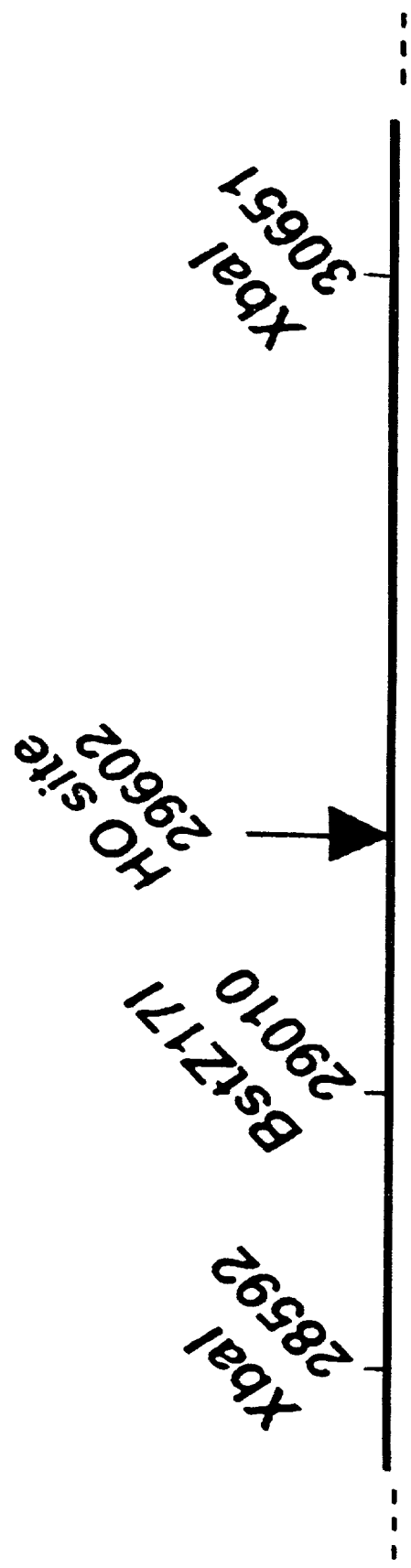

FIGS. 7A–7B Coinfections of E3::HO gene E4 and E3::HO site E4 viruses in nonpermissive A549 cells give rise to dimeric DNA species, but not in permissive W162 cells.

A. Monolayers of cells in 35-mm dishes were infected at a multiplicity of 10 of each virus and harvested after 4 days. Intracellular DNA was isolated from W162 cells infected with E3::HO E4 viruses (lanes 1–3), A549 cells infected with E3::HO E4 viruses (lanes 4–7), or A549 cells infected with E3::HO E4 wild-type viruses (lanes 8–11). The DNA was digested and analyzed as described in the legends to FIGS. 2 and 5. The fragment produced by in vivo HO endonuclease cleavage of the HO site, followed by in vitro digestion with BstZ171 (an isoschizomer of Bst11071), is 595 nt long and is labeled "fragment" to the left of the autoradiogram. The novel band found only in coinfections of nonpermissive A549 cells with the E4 viruses (lanes 6 and 7) is indicated by the arrow. Lane 11 contains XbaI-digested DNA isolated from an E3::HO gene×E3::HO site coinfection of A549 cells. The fragment indicated on the right is the doublet produced by XbaI cleavage of DNA digested in vivo by HO endonuclease.

B. Map of the relevant restriction and HO endonuclease sites. Hybridization was conducted with-probe 1, which contains the XbaI fragment from the E3::HO site virus genome (see FIG. 2C).

Figure 8:
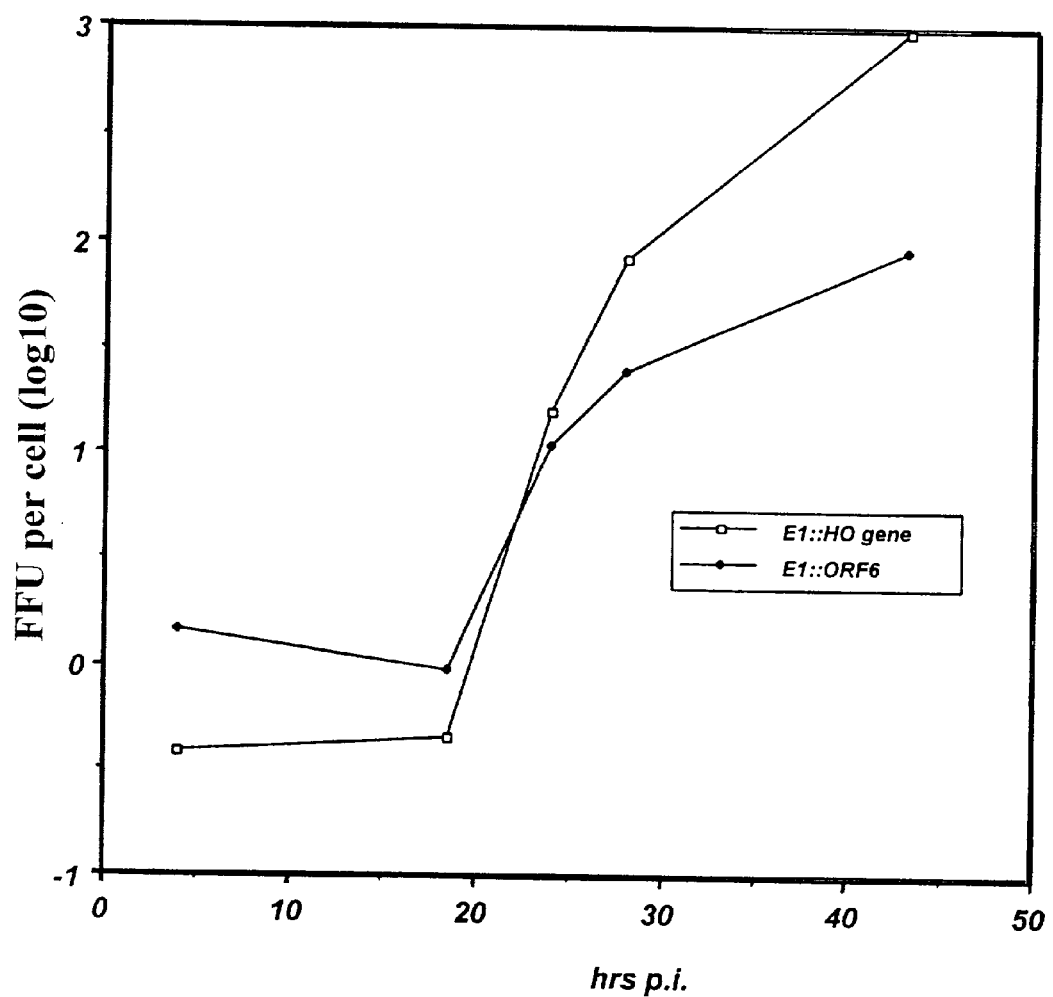

FIG. 8 Replication of Virus VORF6. Open circles, E1:: HO gene; filled circles, E1::ORF6.

Figure 9:
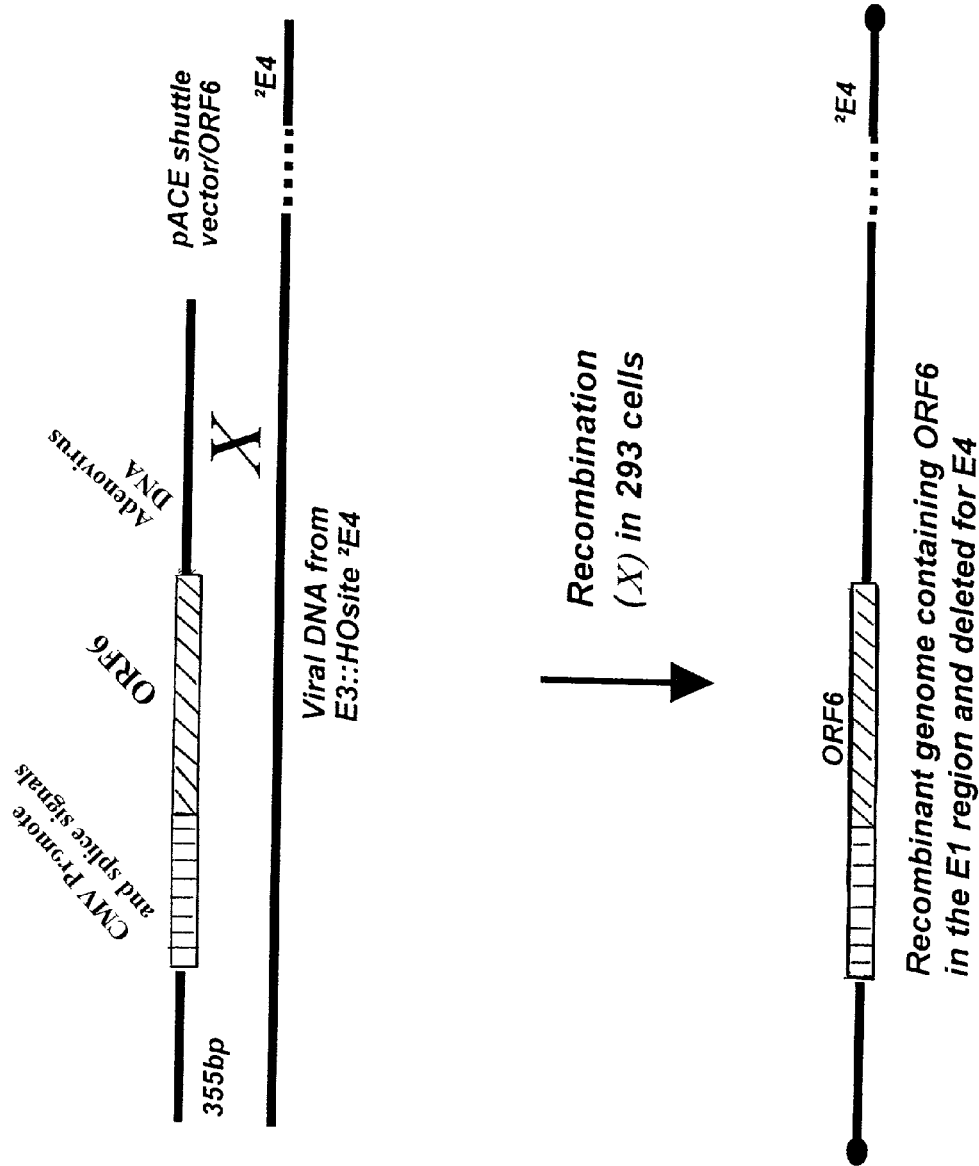

FIG. 9 Construction method for creation of virus E1::E4 ORF6 (VORF6)

Figure 10:
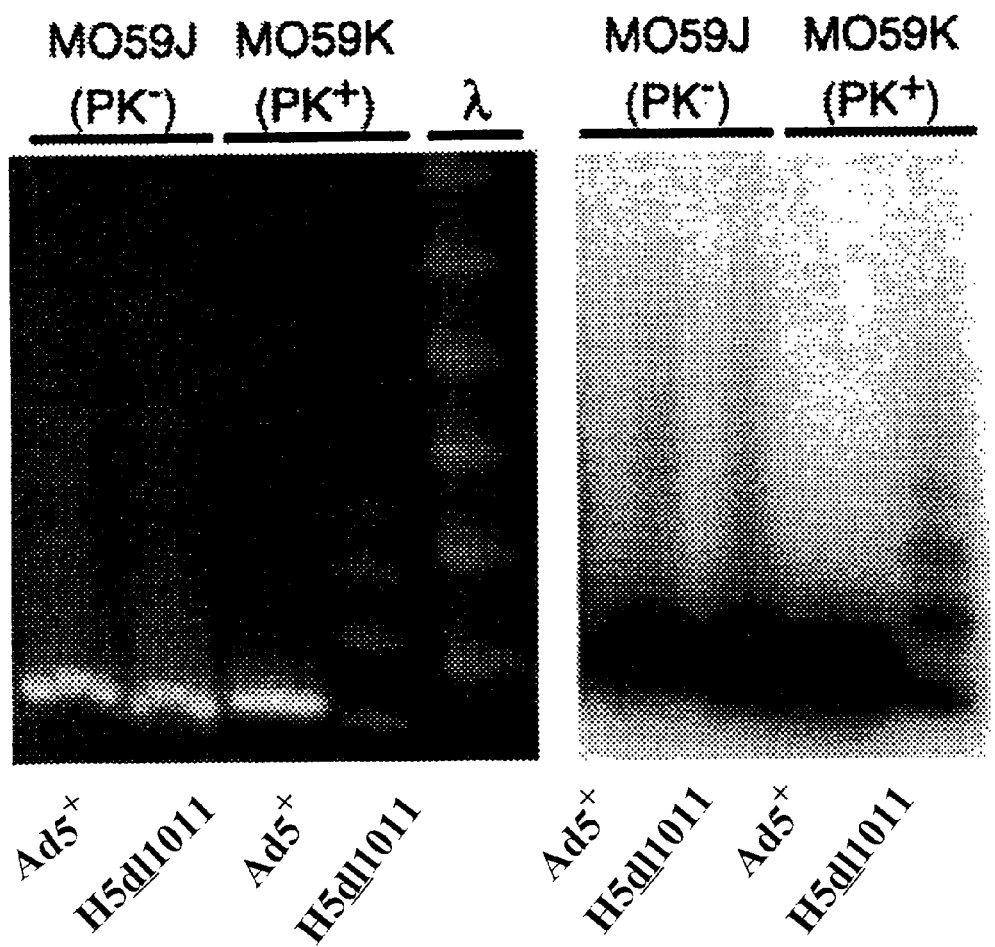

FIG. 10 Adenovirus genome concatemer formation in DNA PK$^+$ and DNA PK$^-$ cells. MO59J (DNA PK$^-$) or MO59K (DNA PK$^+$) cells were infected with either Ad5 or H5dl1011, an E4 mutant lacking all of the recognized E4 open reading frames, at 25 pfu/cell. DNA was prepared from infected cells 52 hours after infection and analyzed by pulsed-field gel electrophoresis (Van der Ploeg et al., 1984). Left panel: photograph of one gel after ethidium bromide staining; right panel: autoradiogram of the same gel after transfer to a nitrocellulose filter and hybridization to $^{32}$P-labeled adenovirus DNA (Southern, 1975, Feinberg and Vogelstein, 1983). The cell line and virus from which DNAs were obtained are indicated for each lane. The genome of Ad5 is about 36 kb; that of H5dl1011 about 33 kb. The lane marked 1 contains concatenated phage lambda DNA (monomer length about 48 kb).

Figure 11A:
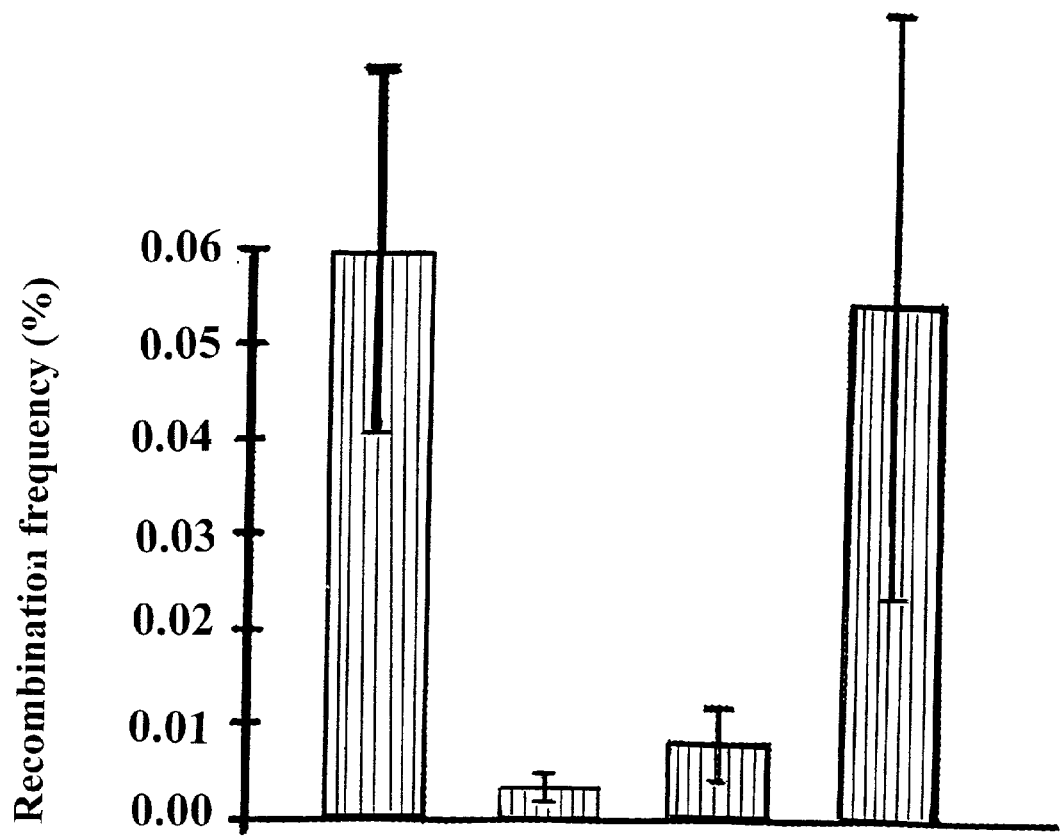
Figure 11B:
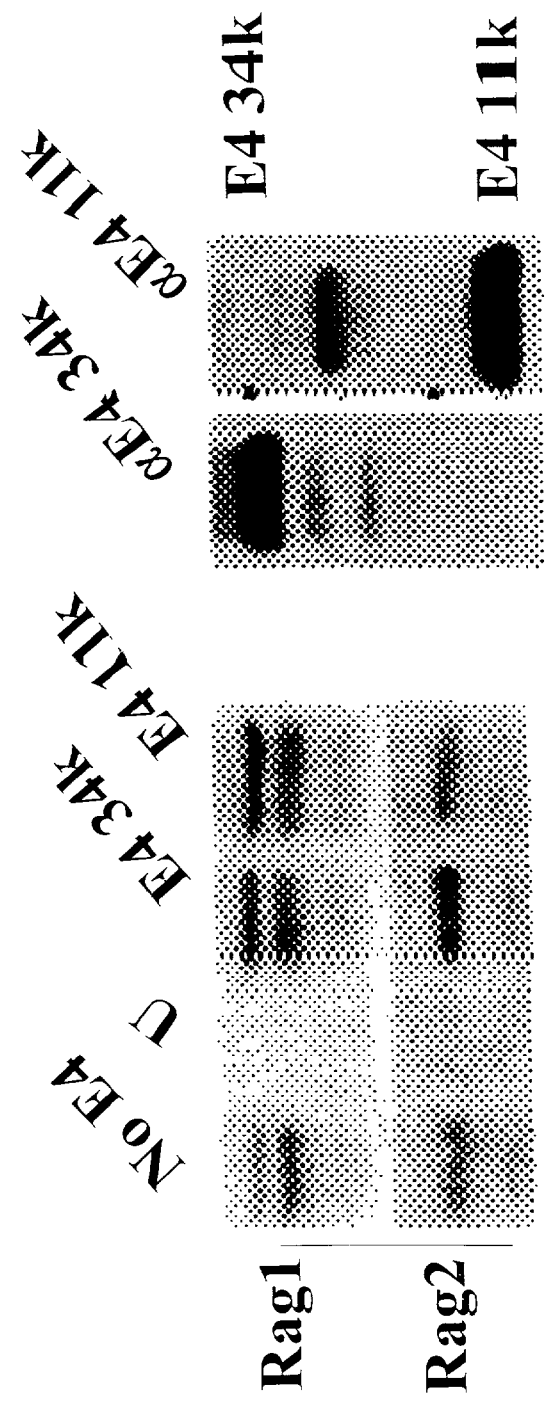

FIGS. 11A–11B Transfection assay of V(D)J recombination in cells expressing of E4 proteins.

A. V(D)J recombination in transfected cells. 293 cells were transfected with JH200, a plasmid substrate for V(D)J recombination, and the indicated combinations of plasmids encoding Rag1, Rag2, E4 34k, and E4 11k. Recombination frequency is given as the percentage of all plasmids recovered from transfected cells that had undergone rearrangement. Error bars indicate standard deviation of the measurements; n indicates the number of determinations for each combination of plasmids.

B. Expression of Rag and E4 proteins in transfected cells. Portions of the transfected cells used in determination of V(D)J recombination frequency (panel A) were analyzed for the expression of Rag1, Rag2, E4 34k, and E4 11k by immunoblotting. Left panel: immunoblots probed with anti-Rag1 (upper) and anti-Rag2 (lower) antibodies. The E4 plasmid present in each transfection is indicated at the top of the lane; the lane marked U contains an extract made from cells that received neither Rag nor E4 plasmids. Right panel: immunoblots probed with antisera to E4 34k or E4 11k, as indicated. The extracts analyzed are those used for the third and fourth lanes of the left panel.

Figures 12A, 12B, 12C:
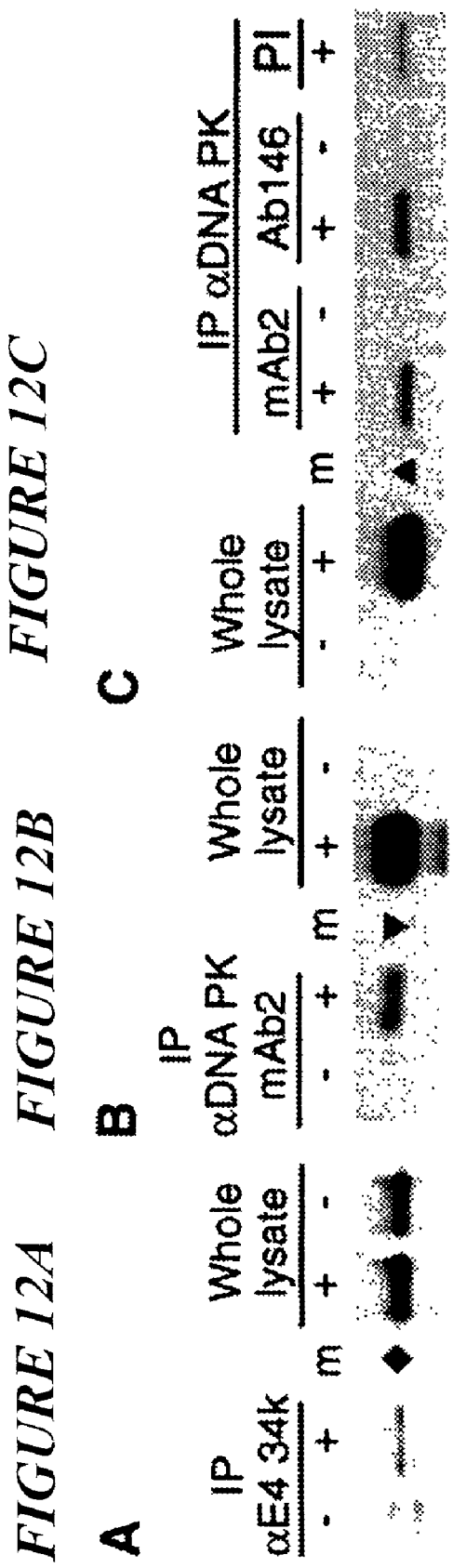

FIGS. 12A–12C Coimmunoprecipitation of DNA PK and the E4 34k and E4 11k proteins.

A. Anti E4 34k antibodies precipitate DNA PK$_{cs}$. Lysates were prepared from 293 cells transfected with either an E4 34k expression plasmid (+) or the empty parental vector plasmid (−) Immunoprecipitates made with anti E4 34k antibody (left side) or unfractionated lysates (right side) were analyzed by immunoblotting with the anti-DNA PK antibody Ab145. The position of DNA PK$_{cs}$ is indicated.

B. Anti-DNA PK antibodies precipitate E4 34k. Lysates were prepared from cells transfected with an E4 34k expression plasmid (+) or the empty parental vector plasmid (−). Immunoprecipitates made with the anti-DNA PK monoclonal antibody mAb2 (left side) or unfractionated lysates (right side) were analyzed by immunoblotting with an anti E4 34k antibody. The position of the E4 34k protein is indicated.

C. Anti-DNA PK antibodies precipitate E4 11k. Lysates were prepared from cells transfected with an E4 11k expression plasmid (+) or empty vector plasmid (−). Immunoprecipitates made with the anti-DNA PK antibodies mAb2 and Ab146 or unfractionated lysates as indicated above the lanes were analyzed by immunoblotting with an anti E4 11k antibody. The lane marked PI contains an immunoprecipitate made with preimmune serum corresponding to Ab146. The position of the E4 11 protein is indicated.

DETAILED DESCRIPTION OF THE INVENTION

The present invention provides a modified adenovirus comprising genomic adenoviral DNA which has been modified so that (i) the only gene product of the early region (E4) that is expressed is open reading frame 6 (ORF-6), (ii)

neither the gene product of the E1A region nor the gene product of the E1B region is expressed, and (iii) no other early or late gene products are expressed.

In an embodiment of the present invention, the modified adenovirus is further modified so that it expresses the gene product of the E1A region of the adenoviral DNA.

In an embodiment of the present invention, the modified adenovirus is further modified so that it expresses the gene product of the E1B region of the adenoviral DNA.

In an embodiment of the present invention, the modified adenovirus is further modified so that it expresses both (i) the gene product of the E1A region and (ii) the gene product of the E1B region of the adenoviral DNA.

As described herein, viruses expressing E4 ORF6 and E1A and/or E1B are constructed using existing viral mutant genomes. The additional genes are expressed using the constitutive CMV immediate early promoter, or by using a di-cistronic construction in which the second gene is expressed via an Internal Ribosome Entry Site (IRES) element.

In an embodiment of the present invention, the modified adenovirus is designated VORF6 (ATCC Patent Deposit Designation Number PTA-2215).

Human adenovirus VORF6 was deposited on Jul. 11, 2000 with the American Type Culture Collection (ATCC), 10801 University Boulevard, Manassas, Va., 20110-2209 U.S.A. under the provisions of the Budapest Treaty On The International Recognition Of The Deposit Of Microorganisms For The Purposes Of Patent Procedure. VORF6 was accorded ATCC Patent Deposit Designation Number PTA-2215.

The present invention provides a method of inhibiting repair of breaks in double-stranded DNA in a cell which comprises introducing into the cell a modified adenovirus comprising genomic adenoviral DNA which has been modified so that (i) the only gene product of the early region (E4) that is expressed is open reading frame 6 (ORF-6), (ii) neither the gene product of the E1A region nor the gene product of the E1B region is expressed, and (iii) no other early or late gene products are expressed.

As described herein, introduction into the cell may be by viral infection.

The present invention provides a method of preventing cancer in a subject which comprises introducing into a cell of the subject a modified adenovirus comprising genomic adenoviral DNA which has been modified so that (i) the only gene product of the early region (E4) that is expressed is open reading frame 6 (ORF-6), (ii) neither the gene product of the E1A region nor the gene product of the E1B region is expressed, and (iii) no other early or late gene products are expressed.

As described herein, the adenovirus prevents the cell from becoming cancerous by inhibiting repair of double-strand DNA breaks in the cell.

The present invention provides a method of treating cancer in a subject which comprises introducing into a cancer cell of the subject a modified adenovirus comprising genomic adenoviral DNA which has been modified so that (i) the only gene product of the early region (E4) that is expressed is open reading frame 6 (ORF-6), (ii) neither the gene product of the E1A region nor the gene product of the E1B region is expressed, and (iii) no other early or late gene products are expressed.

As described herein, the adenovirus prevents cancer cell growth by inhibiting repair of double-strand DNA breaks in the cancer cell, thereby causing death of the cell and treating cancer in the subject.

The present invention provides a method of preventing concatamerization of a linear wild-type adenoviral DNA which comprises introducing into a cell comprising the wild-type adenoviral DNA, a modified adenovirus comprising genomic adenoviral DNA which has been modified so that (i) the only gene product of the early region (E4) that is expressed is open reading frame 6 (ORF-6), (ii) neither the gene product of the E1A region nor the gene product of the E1B region is expressed, and (iii) no other early or late gene products are expressed.

The present invention provides a method of inhibiting V(D)J recombination of nucleic acid sequences encoding immunoglobulins in a cell of the immune system which comprises introducing into the cell, a modified adenovirus comprising genomic adenoviral DNA which has been modified so that (i) the only gene product of the early region (E4) that is expressed is open reading frame 6 (ORF-6), (ii) neither the gene product of the E1A region nor the gene product of the E1B region is expressed, and (iii) no other early or late gene products are expressed.

The present invention provides a method of preventing in a cell apoptosis induced by viral DNA replication in the cell which comprises introducing into the cell, a modified adenovirus comprising genomic adenoviral DNA which has been modified so that (i) the only gene product of the early region (E4) that is expressed is open reading frame 6 (ORF-6), (ii) neither the gene product of the E1A region nor the gene product of the EBB region is expressed, and (iii) no other early or late gene products are expressed.

The present invention provides a method of increasing efficiency of chemotherapeutic or radiation treatment of cancer in a subject which comprises: a) introducing into cancer cells of the subject a modified adenovirus comprising genomic adenoviral DNA which has been modified so that (i) the only gene product of the early region (E4) that is expressed is open reading frame 6 (ORF-6), (ii) neither the gene product of the E1A region nor the gene product of the E1B region is expressed, and (iii) no other early or late gene products are expressed; and b) administering a chemotherapeutic agent or radiation to the subject.

As described herein, the chemotherapeutic agent or radiation may operate by causing breaks in double-stranded DNA of a cancer cell.

In an embodiment of the present invention, the adenovirus is introduced into the cancer cells before the chemotherapeutic agent or radiation is administered to the subject.

In an embodiment of the present invention, the adenovirus is introduced into the cancer cells after the chemotherapeutic agent or radiation is administered to the subject.

In an embodiment of the present invention, the adenovirus is introduced into the cancer cells concurrently with administering the chemotherapeutic agent or radiation to the subject.

In an embodiment of the present invention, the chemotherapeutic agent is cisplatin or doxorubicin.

In one embodiment of any of the methods described herein, the modified adenovirus is further modified so that it expresses the gene product of the E1A region of the adenoviral DNA. In one embodiment, the modified adenovirus is further modified so that it expresses the gene product of the EBB region of the adenoviral DNA. In one embodiment, the modified adenovirus is further modified so that it expresses both (i) the gene product of the E1A region and (ii) the gene product of the EBB region of the adenoviral DNA. In one embodiment, the modified adenovirus is designated VORF6 (ATCC Patent Deposit Designation Number PTA-2215).

The present invention provides a method of inhibiting repair of breaks in double-stranded DNA in a cell which comprises introducing into the cell the gene product of the early region 4 (E4) open reading frame 6 (ORF-6) of genomic adenoviral DNA.

As described herein, introduction of the gene product into the cell may be accomplished by transfection with a plasmid which expresses the gene product, by introduction of a virus which expresses the gene product, by introducing the protein directly into the cell, or by any other means known to one of skill in the art.

The present invention provides a method of preventing cancer in a subject which comprises introducing into a cell of the subject the gene product of the early region 4 (E4) open reading frame 6 (ORF-6) of genomic adenoviral DNA.

As described herein, the gene product prevents a cell from becoming cancerous by inhibiting repair of double-strand DNA breaks in the cell.

The present invention provides a method of treating cancer in a subject which comprises introducing into a cancer cell of the subject the product of the early region 4 (E4) open reading frame 6 (ORF-6) of genomic adenoviral DNA.

As described herein, the gene product prevents cancer cell growth by inhibiting repair of double-strand DNA breaks in the cell, thereby causing death of the cell.

The present invention provides a method of preventing concatamerization of a linear wild-type adenoviral DNA which comprises introducing into a cell comprising the wild-type adenoviral DNA, the product of the early region 4 (E4) open reading frame 6 (ORF-6) of genomic adenoviral DNA.

The present invention provides a method of inhibiting V(D)J recombination of nucleic acid seqeuences encoding immunoglobulins in a cell of the immune system which comprises introducing into the cell, the product of the early region 4 (E4) open reading frame 6 (ORF-6) of genomic adenoviral DNA.

The present invention provides a method of preventing in a cell apoptosis induced by viral DNA replication in the cell which comprises introducing into the cell, the product of the early region 4 (E4) open reading frame 6 (ORF-6) of genomic adenoviral DNA.

The present invention provides a method of increasing efficiency of chemotherapeutic or radiation treatment of cancer in a subject which comprises: a) introducing into cancer cells of the subject the product of the early region 4 (E4) open reading frame 6 (ORF-6) of genomic adenoviral DNA, and b) administering the chemotherapeutic agent or radiation to the subject.

As described herein, the chemotherapeutic agent or radiation may operate by causing breaks in doublestranded DNA of the cell.

In an embodiment of the present invention, the product of the early region 4 (E4) open reading frame 6 (ORF-6) of genomic adenoviral DNA is introduced into the cancer cells before the chemotherapeutic agent or radiation is administered to the subject.

In an embodiment of the present invention, the product of the early region 4 (E4) open reading frame 6 (ORF-6) of genomic adenoviral DNA is introduced into the cancer cells after the chemotherapeutic agent or radiation is administered to the subject.

In an embodiment of the present invention, the product of the early region 4 (E4) open reading frame 6 (ORF-6) of genomic adenoviral DNA is introduced into the cancer cells concurrently with administering the chemotherapeutic agent or radiation to the subject.

In an embodiment of the present invention, the chemotherapeutic agent is cisplatin or doxorubicin.

This invention will be better understood from the Experimental Details which follow. However, one skilled in the art will readily appreciate that the specific methods and results discussed are merely illustrative of the invention as described more fully in the claims which follow thereafter.

Experimental Details

First Series

Because double-strand DNA breaks (DSBs) are lethal, all mammalian cells contain active systems to repair DSBs. To investigate mechanisms of DSBR in mammalian cells, an adenovirus-based system for the efficient production of double-strand DNA breaks has been developed. The system consists of genetically-engineered adenoviruses which contain the gene for the yeast-derived site-specific HO endonuclease, and adenoviruses that contain the HO endonuclease target site. When an HO gene virus and an HO site virus are introduced simultaneously into human cells, DSBs are induced at the HO cleavage sites in the target virus. Despite the presence of systems for DSBR, the expected rejoining of the cleaved genomes is not observed in these experiments if the vectors express early region 4. Ablation of E4 activity in the infecting viruses by the deletion of E4 sequences permits repair of the HO-induced breaks, indicating that an E4 product (or one dependent upon E4) inhibits DSBR. This was confirmed by the observation that, in cells infected with E4-deleted HO gene and HO site viruses, addition of a virus expressing the E4 34k product alone was sufficient to prevent rejoining of the HO-produced DSBs. As disclosed herein, the E4 ORF6 product inhibits DSBR.

Adenovirus Vectors Containing the Yeast HO Endonuclease Gene or the HO Recognition Site A set of vectors was created in which DSBs could be created at high efficiency in a coinfection with two adenoviruses, one expressing a specific endonuclease and the other containing a single recognition site for that endonuclease. The mating-type switch HO endonuclease of S. cerevisiae is particularly suitable for this approach. First, in its native species, the recognition site is large, well characterized, and recognized at ectopic locations; second, the endonuclease can be expressed under heterologous promoters giving considerable flexibility in experimental design. Although a recent report shows that HO endonuclease is functional in plant cells (Chiurazzi et al., 1996), it was not known whether this would be true in mammalian cells because it was possible that yeast-specific accessory factors (Wang et al., 1997) might be necessary for its activity and site-specificity. Alternatively, factors present in mammalian cells might inhibit its activity, or the structure of the target genome might render it inaccessible to enzyme action. Finally, overexpression of the HO gene might be lethal to the cell, making it impossible to create the appropriate adenovirus vector. Fortunately, adenovirus vector design is sufficiently flexible to allow the construction of recombinant viruses expected to express different levels of HO endonuclease and with different temporal onset. In addition, two different locations for the HO site could be used, in case the local sequence in the target genome influenced activity and specificity of cleavage.

The HO-expressing viral vectors were created in two stages. First the cDNA for the HO gene was placed either in early region 3 of plasmid pPF446, where it would be under the control of the adenovirus early region 3 promoter, or in plasmid pAdCMV (Falck-Pedersen et al., 1994), where it would be controlled by the cytomegalo-virus immediate-early promoter and enhancer (Akrigg et al., 1985). Second, the two expression cassettes were transferred into virus using in vivo recombination either with restriction-cut DNA protein complex from virus LLX1 (Brunet et al., 1987) or with the large construction plasmid pJM17 (McGrory et al., 1988). Essentially similar strategies were used to create viruses with the HO site embedded in either E1 or E3, except that the E1 HO site virus was created by overlap recombination with XbaI-digested DNA from a derivative of virus dIE3 (Gall et al., 1996). The design of the transfer cassettes and the placement of the HO gene and HO site are shown in FIGS. 1A–1D. All four viruses were obtained easily and replicated to high titer in the appropriate cell lines. This indicates that the insertions of foreign DNA into the viral genome do not disrupt essential functions and suggests that the expected expression of the HO endonuclease is not toxic to the infected cells, at least under transient conditions of a viral infection.

The HO Site Located in the E3 Region can be Cleaved by HO Endonuclease-Expressing Adenovirus Vectors The first goal was to determine whether the HO gene located in the E3 region can be expressed and can cleave the HO site (also located in E3) in a viral genome introduced by coinfection. A549 cells were coinfected with the Ad E3::HO gene and Ad E3::HO site and intracellular DNA was isolated at intervals by a modification of the Hirt (1967) technique. Following digestion by XbaI, the DNA fragments were separated on an agarose gel and analyzed by Southern transfer-hybridization using a probe (see FIG. 2C) that encompassed the E3::HO site. The results (FIG. 2A) show that there is the expected increase in DNA corresponding to both parents and the appearance of a novel band of ~1 kbp (arrow), whose size is consistent with cutting of the Ad E3::HO site genome by the HO endonuclease. (The two fragments of 1016 and 1051 nt in length produced by subsequent XbaI digestion comigrate in this gel system.) The DNA samples were also analyzed in the absence of XbaI digestion and a novel band of ~6.5 kbp was observed in the coinfection. Further analyses with a variety of restriction digestions and probes showed unequivocally that the novel band arose from cutting at the HO site (see FIGS. 4, 5, and 7 for further evidence). Most importantly, the band was never observed in single infections with either the HO gene virus or the HO site virus (FIG. 2A, lanes "gene" and "site") or in coinfections with the HO gene virus and the isogenic parent of the HO site virus. Thus, the yeast HO endonuclease expressed in mammalian cells is capable of recognizing and cleaving a yeast HO site embedded in the viral genome. Quantitation of the XbaI fragments from both parental genotypes and the HO-cleaved fragments shows that the cleaved material can be detected at 12 hour postinfection (p.i.) and the absolute amount increases somewhat faster than the increases in the parental species from about 4% of the total at 15 hour p.i. to an average of about 30% after 21 hour p.i. (FIG. 2B).

The percentage of parental DNA cleaved in the Ad E3::HO gene X Ad E3::HO site coinfections in different experiments has ranged from 10 to 40%. There are several possible reasons for this plateau value, including achievement of a steady state between cleavage and rejoining of the broken molecules, limited expression from the E3 region of an endonuclease that in vitro displays stoichiometric kinetics of cleavage (Jin et al., 1997), and an inaccessibility of a proportion of the population of viral genomes to cleavage. Lack of accessibility could be caused by a temporal change in the structure of the target and/or by removal of unbroken genomes by packaging. To address the question of lack of adequate expression of the HO gene, A549 cells were coinfected with the Ad E1::HO gene and Ad E3::HO site viruses, either simultaneously or with the E1::HO gene virus preinfecting the cells for 24 h, followed by the E3::HO site virus. Infected cells were harvested at intervals after the E3::HO site infection. In both coinfections the HO gene is under the control of the immediate-early CMV promoter and the gene should be expressed at high levels immediately upon infection. However, neither coinfection showed evidence for an increase in cutting of the HO site located in E3, compared with an E3::HO gene and E3::HO site virus coinfection (FIG. 3; compare 24 hour lanes). The E3::HO site genome was cleaved by 8 hour p.i. in the E1::HO gene preinfection sample, whereas no cutting could be detected in the simultaneous coinfection at that time, even after longer exposures of the filter. This finding suggests that temporal changes in the structure of the viral template may play some role in accessibility, but the magnitude of the effect is not great. Further experiments to see whether the level of HO gene expression could affect the degree of cutting included increasing the multiplicity of infection (m.o.i.) of the E3::HO gene virus relative to the E3::HO site virus. No quantitative effects were detected. Taken together, these results suggest that the observed upper limits of cutting are not determined solely be a lack of expression of the HO endonuclease.

Adenovirus Genome Fragments can be Packaged into Viral Particles

As mentioned above, packaging of viral genomes could affect the accessibility of potential targets and might influence the percentage of broken fragments observed at late times. For example, if some genomes have not been cleaved, or have been cleaved and repaired, at the time assembly begins, packaging into virions will remove these genomes from the pool of potentially cleavable molecules. On the other hand, if broken fragments are packaged, they will be removed from the pool of reparable fragments. These two possibilities are not mutually exclusive, but they will have opposite effects on the observed frequency of broken fragments.

To address the possibility that packaging might remove broken fragments from the intracellular pool, A549 cells were coinfected with the Ad E3::HO gene and Ad E3::HO site, and DNA was isolated directly from the infected cells or from CsCI-purified virus from the same sample of infected cells. The DNAs were digested with XbaI and examined by Southern transfer hybridization using two different probes (FIG. 4). Probe 1 recognizes the intact XbaI fragment and the two fragments created by HO cleavage, whereas probe 2 is limited to sequences distal to the HO cleavage site and thus recognizes the intact XbaI fragment and only the distal cleaved fragment. The results in FIG. 4A demonstrate two points. First, the purified virus preparation contains a significant percentage of DNA cleaved by HO, because the larger probe hybridizes not only to the intact XbaI species but also to the species of ~1 kbp produced by HO cleavage. Thus a considerable number of broken fragments are removed from the intracellular pool and presumably cannot be repaired. Second, probe 2 hybridizes to both the HO-cleaved and uncleaved XbaI fragments in the intracellular DNA, but it hybridizes only to the uncleaved fragment in the purified virus DNA preparation. Thus the rightward fragment produced by intracellular HO cleavage is not packaged into virions. Because the packaging signal is located at the left-hand end of the genome (Hammarskjold and Winberg, 1980; Grable and Hearing, 1992; Schmid and Hearing, 1997) and right-hand end fragments could be incorporated into virions only if they were attached to the left-hand end fragments, this result suggests that the two genomic fragments produced by HO cleavage are not held together tightly enough to proceed through the packaging process.

The Broken Fragments Produced by Cleavage at the E3 Site are not Joined Efficiently in Trans One of the main purposes in developing the HO endonuclease adenovirus vectors was to create double-strand breaks in vivo and to follow their repair under a variety of experimental conditions. Having shown that DSBs can be made, the next step was to gain evidence for rejoining. In theory, joining could recreate a unit length molecule, and depending on the fidelity of the rejoining reaction, the HO site would be reformed. In addition, rejoining could occur in trans between two left-hand or right-hand end fragments to form two types of large inverted dimeric molecules.

To test the possibility of unfaithful rejoining of the HO site, 10 independent coinfections with the Ad E3::HO site and Ad E3::HO gene were set up, and intracellular DNA was isolated at late times from 9 of the samples. This DNA was subjected to PCR amplification using primers flanking the inserted HO site sequence. Gel electrophoresis of the amplified sequence showed a uniform specie of a size expected from amplification of the wild-type HO site. To examine individual molecules, the PCR products were cloned and sequenced. The 35 cloned sequences examined were identical to that of the wild-type HO site. Infectious virus present in the 10$^{th}$ coinfected sample was harvested, and the virus was repassaged to uninfected cells, to see whether there was any evidence for selection of genomes that are unable to be cleaved by the HO endonuclease. Again, intracellular DNA was isolated at late times, PCR-amplified, cloned, and sequenced. Twelve clones were examined and all had the wild-type HO site. Taken together, these results indicate either that rejoining of the HO half sites to form a unit length genome is always faithful or that the cut molecules are very rarely rejoined and that the PCR amplification occurs on genomes that have not been cleaved during the course of infection.

The possibility that broken fragments can rejoin in trans was tested by restricting the DNA with either XhoI or Bst1107I, whose sites are located on either side of the HO site (FIG. 5B). Note that because the HO site is nonpalindromic and is cleaved to give a 3' overhanging end, rejoining of two identical fragments will necessarily result in the creation of a novel sequence and the likely loss of some nucleotides. Southern hybridization of DNA restricted with these two enzymes (FIG. 5) showed the presence of the expected XhoI and Bst1107I fragments (arrows), resulting from HO endonuclease action in the infected cells, but no evidence for the expected end-joined products, even on long exposure of the autoradiograph. This result suggests that joining in trans is a rare phenomenon, even though the mammalian cell has very active DSB repair activities capable of joining noncohesive DNA end structures (Roth and Wilson, 1988). These results can be taken to indicate either that the ends created by HO endonuclease are inaccessible to the repair machinery or that virus infection inhibits the mechanism. Results presented below suggest that the latter idea is the more likely.

An HO Site Located in the E1 Region can be Cleaved by HO Endonuclease, Under Both Permissive and Nonpermissive Conditions of Viral Replication Another possible explanation for the limit to fragment formation observed in the coinfections with the Ad E3::HO site and Ad E3::HO gene viruses (FIG. 2B) is that the frequency of cleavage may be limited by the accessibility of the site in E3. To test this directly, a virus with the site located in the E1 region was constructed and crossed with the Ad E1::HO gene virus. Cleavage by HO will liberate a left-hand end fragment 450 nt long. Initial experiments were performed under permissive conditions in 293 cells. Intracellular viral DNA was isolated and following in vitro digestion with BstBI, the DNA was analyzed by Southern transfer-hybridization (FIG. 6, lane 1–3). The results show that the HO site in E1 is cleavable ("cut" fragment in lane 3). Repeated experiments have demonstrated that the steady-state level of E1 site cleavage in 293 cells is between 5 and 20%, somewhat lower than the range of 10–40% seen with the site in E3 assayed in A549 cells. Similar values were observed in crosses between the Ad E1::HO site and the Ad E3::HO gene in A549 cells, again supporting the suggestion made above that the degree of cutting of the HO site is probably not limited by the levels of expression of the HO endonuclease.

One possibility for the low level of apparent cutting at the E1::HO site is that the left-hand end of the genome may become associated with proteins necessary for assembly into mature virus particles. This is plausible given that the packaging signal is located toward the left-hand end (Hammarskjold and Winberg, 1980; Grable and Hearing, 1992; Schmid and Hearing, 1997) and that the left-hand end is preferentially incorporated into incomplete particles (Chee-Sheung and Ginsberg, 1982). To test the level of cutting under nonpermissive conditions, the coinfection with Ad E1::HO site and Ad E1::HO gene viruses was repeated in A549 cells, and the intracellular DNA was isolated at intervals after infection, digested in vitro with BstBI, and then analyzed by Southern transfer-hybridization. As shown in FIG. 6 (lanes 4–8) not only was the expected cut band observed, but also a novel species of about 900 bp (arrow). This novel species, which increased in abundance at later times, was not seen in coinfections in 293 cells. Further analysis of the viral DNA with a variety of restriction enzymes and probes demonstrated that the 900-bp species is an inverted dimer of the cut species. This is most likely to arise from end-joining of two individual fragments. Note that the size range of this novel species appears to be quite uniform, suggesting that most of the end-joining occurs by a precise mechanism and that few nucleotides are lost, as suggested from previous results with transfected DNA [reviewed in Roth and Wilson (1988)]. It should also be pointed out that the accumulation of cut and joined species reached some 90% of the total of E1::HO site genome DNA, compared to the lower levels seen with E1 cross in permissive 293 coinfections. Analysis with probes complementary to the larger right-hand end fragments demonstrated that they also formed dimer species. These results suggest that DSBR can occur if expression of E1 products is absent, and they indicate that E1 acts directly or indirectly to inhibit end-joining. It is important to note that these observations are not limited to A549 cells, as very similar results have been obtained in nonpermissive HeLa and KB cell derivatives.

E4 Products Inhibit DSBR

The results with the E1::HO virus coinfections in A549 cells could be explained if E1 products themselves inhibit end-joining or if E1A is necessary to induce downstream viral products that are the inhibitory factors. Weiden and Ginsberg (1994) showed that infections of E4 deletion viruses in nonpermissive human KB cells exhibited genome concatemer formation, and one possible interpretation of their observations is that E4 products inhibit the end-joining of adenovirus genomes. To test this with the HO system, two further viruses were created, Ad5 E3::HO gene E4 and Ad5 E3::HO site E4, both of which contain the major E4 deletion present in H5dI366 (Halbert et al., 1986). Nonpermissive A549 or permissive W162 cells (Weinberg and Ketner, 1983) were infected with these viruses, and intracellular DNA was examined by Southern hybridization following digestion with BstZ17I. A novel band of approximately 1.2 kb was observed in samples from coinfections of A549 cells with the E4 deleted viruses (FIG. 7, duplicate samples in lanes 6 and 7, arrow) and not in the permissive W162 cells (lane 3) or in parallel infections of E3::HO E4 wild-type viruses in A549 cells (lane 10). Thus, eliminating E4 expression leads to detectable DSBR activity. These results suggest that one or more E4 products inhibit end-joining and, by inference, that the failure to inhibit this activity is one of the causes of genome concatemer formation in E4 deletion infections (Weiden and Ginsberg, 1994). As with the crosses involving the E1::HO viruses in nonpermissive cells, the end-joined species seems to be uniform in size, again suggesting a precise mechanism. This is in contrast to the genome concatemer junctions, which are much more heterogeneous (Weiden and Ginsberg, 1994).

Construction of Viruses Expressing E4 ORF-6 and E1A and/or E1B

Viruses expressing E4 ORF6 and E1A and/or E1B are constructed using existing viral mutant genomes (as described herein). E1A and/or E1B are expressed from the left hand end of the viral genome under the control of a separate promoter (the constitutive CMV immediate early promoter), or by use of a di-cistronic, IRES-containing gene sequence. In the di-cistronic construction, the second gene is expressed via an Internal Ribosome Entry Site (IRES) element.

Construction and Characteristics of Virus E1::ORF6 (VORF6)

An adenovirus vector was constructed which expresses early region 4 ORF6 protein, in the absence of expression of any other adenovirus gene. Although a complete deletion of early region 4 (E4) of adenovirus aborts the infectious cycle at the late stage of infection, expression of the ORF6 protein encoded by E4 is sufficient to restore full virus replication. The virus lacks the E4 region, and an ORF6 coding sequence expression cassette, controlled by the constitutive human cytomegalovirus (CMV) immediate early promoter, replaced the E1 region. This virus is capable of replicating in human 293 cells, which contain and express the E1 region proteins necessary for a successful infection, because ORF6 is expressed from the cassette. Most importantly, as the native E4 region is deleted, the only E4 protein expressed is ORF6. Thus the functions of ORF6 can be tested in a variety of non-permissive cell lines and in a number of different experimental protocols, without the possible confounding effects of any "leaky" expression from other E4 functions if the E4 region were to remain intact. The vector was designed with the expectation that ORF6 would be expressed at high levels from the beginning of the infection. In the context of this patent disclosure, the role of ORF6 in inhibiting double strand break repair was demonstrated in isolation from other viral gene products. The construction of the virus is shown in FIG. 9 and described below.

The genomic structure was analyzed by restriction digestion of DNA isolated from infected 293 cells. The genome contained the ORF6 cDNA under CMV promoter control, and the cassette was located in the E1 region. Monoclonal antibody analysis of infected cell protein extracts showed that ORF6 protein was expressed. A one-step replication cycle analysis showed that the final yield of virus was lower than that of a virus of similar overall structure, but containing a different gene in the E1 region (see FIG. 8). The virus was capable of replication in complementing 293 cells, but could replicate neither in human A549 cells, which lack E1 genes and therefore fail to express E1 proteins, nor in W162 cells a cell line expressing E4 proteins (Weinberg and Ketner, 1983).

Inhibition of DSB Repair in Viral Infection

The virus disclosed herein was used to demonstrate that ORF6 inhibits the joining of DNA double strand breaks created in viral genomes by the yeast HO endonuclease. Human A549 cells were infected with the pair of viruses E3::HO site delta E4 and E3::HO gene delta E4. The HO recognition site is cleaved upon expression of HO endonuclease and the broken ends can be rejoined by the cellular non-homologous end joining (NHEJ) machinery. If the A549 cells are also infected with vORF6, the amount of joined product is very much reduced or absent. This triple infection, in which the only E4 protein to be expressed is ORF6, establishes that ORF6 protein is capable of inhibiting DSB repair by the NHEJ machinery. Note that in this experiment, early gene products from the E1 and E2 regions were expressed in the infected cells. Similarly in the transfection experiments conducted by Boyer et al. (1999) to demonstrate inhibition of immunoglobulin gene rearrangement by ORF6, the 293 cells used expressed E1 proteins. In addition, co-infection with vORF6 is incapable of inhibiting the repair of double strand breaks observed when A549 cells are infected with E1::HO site and E1::HO gene viruses. This suggests, but does not prove, that ORF6 may need to act in concert with other viral protein(s) to inhibit NHEJ. The most likely candidate for this would be the E1B 495R (55 kDa) protein, known to interact physically and functionally with ORF6 (Halbert et al., 1986; Sarnow et al., 1984). This possibility is being actively pursued by the creation of viruses expressing the 55 kDa alone, or by the use of cell lines expressing this protein.

Therapeutic Uses of the VORF6 Virus

Non-homologous end joining (NHEJ) is thought to be the main pathway for the repair of double strand breaks in mammalian cells [see for example Wang et al., (2001)] although repair via homologous recombination can undoubtedly take place [see for example (Dronkert et al., 2000; Johnson and Jasin, 2000)]. Thus ORF6 expression, either alone or in concert with other viral proteins, where sufficient to inhibit NHEJ, would prove a useful therapeutic tool. Precedent for the use of adenovirus as a tumor therapy vector expressing a desired transgene or a specific subset of viral proteins has been established. Recent examples include Nemunaitis et al., (2000, 2001); Eck et al., (2001), and there is every reason to believe that various types of adenovirus vector will become a part of the oncologists' armamentarium. It should be emphasized that the virus expressing ORF6 can be used in conjunction with well-established chemotherapeutic agents such as cis-platin, or ionizing radiation treatments, that induce double strand breaks. The inhibition of NHEJ by ORF6 would then be expected to lower the survival of the tumor cells below that observed with chemotherapy or ionizing radiation alone. Precedent for the efficacy of joint treatments with virus and chemotherapy has come from a recent phase two trial of the use of adenovirus ONYX015 and cis-platin in the treatment of refractory head-and neck tumors (Khuri et al., 2000) and with other chemotherapies involving an adenovirus vector expressing p53 as a treatment for small cell lung carcinoma (Schuler et al., 2001). The virus can be injected directly into the tumor, which may be inoperable, or for example into the hepatic portal vein for liver tumor.

The present application demonstrates that the 34 kDa protein encoded by adenovirus early region 4 (E4) inhibits double-strand break repair (DSBR) in mammalian cells. The E4 34k protein is the first protein shown to be capable of inhibiting DSBR. DSBR is important in preventing malignancy, and E4 34k may be useful in modulating DSBR for preventative or therapeutic purposes. In addition, the E4 34k protein may be the prototype of a family of proteins that can inhibit DSBR. Because inactivation of the DSBR system predisposes to cancer, cellular proteins that are functionally homologous to E4 34k may represent a new class of cellular oncogenes.

Prior to this study, the use of adenovirus to study double-strand break repair had been limited either to the analysis of fragments of viral DNA transmitted to the cell by the relatively inefficient method of transfection (Volkert et al., 1989; Volkert and Young, 1983; Mautner and Mackay, 1984) or to the analysis of the capacities of normal and repair-deficient cell types to reactivate DNA damaged by a variety of agents capable of making DNA adducts or single- or double-strand breaks [for a recent example see Rolig et al. (1997)]. In contrast, the facility with which adenovirus can be used as a vector has not been exploited comprehensively to study repair phenomena, even though this is a very promising approach.

Adenoviral vectors have been made in which the yeast mating-type switching HO endonuclease is expressed from the E3A region under E3 promoter control, or from the E1 region under CMV IE promoter control. Companion viruses were created in which the HO recognition site was placed in the E1 or E3 regions. In co-infections with an HO gene and an HO site virus, under fully permissive conditions of replication, up to 30% of the target genomes were cleaved. However, no evidence for rejoining of the broken molecules could be obtained. One possibility for the apparent lack of re-joining is that the cellular DSB-repair mechanism(s) are inhibited by adenovirus-encoded or induced functions. This idea was reinforced when it was observed that co-infections with E1-deleted viruses, under non-permissive conditions in which all viral functions are expressed at low or non-existent levels, did show evidence for DSB repair. A clue that the inhibition might be a function of the E4 region derived from earlier results of Weiden and Ginsberg, (PNAS 91:153) who showed that non-permissive cells infected with viruses that had deletions in E4 contain large concatemers of the viral genome. One interpretation of this observation is that one or more functions encoded by E4 inhibit DSB repair, directly or indirectly.

To test this, the viruses in which the HO gene and HO site are located in E3 were reconstructed to contain large E4 deletions. Co-infection of these E4$^-$ derivatives under non-permissive conditions showed that DSB repair was no longer inhibited, in contrast to the results with their E4$^+$ progenitors. This strongly suggests that one or more functions of E4 are responsible for the inhibition of DSB repair. To determine which E4 functions are involved, and the possible mechanisms, viral vectors were created in which single E4 ORFs are expressed from the E1 region of the virus. Specifically, the effects of the expression of E4 ORF6 and ORF3 on DSB repair were investigated because either of these two ORFs were shown by Weiden and Ginsberg to inhibit concatemer formation.

In mixed infections with HO gene and site viruses, cleavage at the HO site was observed, but rejoining of the singly cleaved genomes could not be detected unless the E4 region was either deleted or not expressed. These observations suggested that one or more functions encoded by E4 inhibit DSB repair, directly or indirectly, consistent with earlier results from Weiden and Ginsberg showing that viral genomes of E4-deleted viruses formed concatemers in non-permissive cells. Concatemer formation could be inhibited by either pORF3 or pORF6 alone, another example of the overlap in function of these two ORFs.

To test the role of individual E4 ORFs in the inhibition of DSB repair, A549 cells were triple-infected with HO gene and site viruses and one of a set of different viruses expressing E4 ORF3 or E4 ORF6. Inhibition by pORF6 was different viruses expressing E4 ORF3 or E4 ORF6. Inhibition by pORF6 was tested using a derivative of mutant dl366, in which the ORF6 gene was located in the E1 region under CMV IE promoter control. Inhibition of DSB repair was evident in infections involving E3::HO gene and site viruses, but not in those using E1::HO gene and site viruses. In the former case, viral DNA replicated and late proteins were produced because of complementation by pORF6, whereas in the latter case very low levels of early and late gene expression were expected to occur. Parallel triple infections were conducted with viruses expressing ORF3 either from the E4 region (virus dl366*ORF3, from Pat Hearing) or from E1 (a pJM17 derivative from Richard Marcellus). In neither case was inhibition of DSB repair observed. These results contrast with the observations on the inhibition of concatemer formation, and suggest that pORF6 is better able to inhibit DSB repair. This inhibition is unlikely to be caused indirectly by the accumulation of late gene products, because the triple infection with dl366*ORF3 allowed high levels of late protein expression, yet no inhibition was observed. Nevertheless, although pORF6 is necessary for inhibition, it is not sufficient (at least under the conditions of the E1::HO gene and site experiment) suggesting that it may need to act in concert with other early gene products, or with cellular proteins induced by them. Preliminary evidence suggests that the ORF6-interacting E1B 495R protein is not sufficient in addition to pORF6 to allow inhibition.

The results presented here show that adenovirus vectors expressing the yeast mating-type switch HO endonuclease can be used to create DSBs in other viral genomes containing the HO recognition site, that the broken fragments containing a packaging signal can be incorporated into complete virus particles, and, in certain circumstances, that they can rejoin in trans. Thus adenovirus vectors can be used to investigate DSB repair, and it is likely that this will be true under a range of experimental conditions and in a wide variety of cell types. As an obvious example, it will be of some interest to use this vector system to examine the capacities of cell lines known or expected to be deficient in various aspects of DSB repair [for recent reviews see Jeggo (1998), Zdzienicka (1999), and Kanaar et al. (1998)].

The observation that a viral genome containing an HO site can be cleaved by the HO endonuclease expressed from a coinfecting adenovirus demonstrates that no other yeast-specific cofactor is required for enzymatic action in mammalian cells. Whether the activity could be increased by such factors is currently unknown, but it has been shown that sequences surrounding the minimum recognition site enhance the cleavability of the site and that protein factors bind to these flanking sequences (Wang et al., 1997). Moreover, the activity of the purified endonuclease has been shown to be inefficient and that the enzyme is required in stoichiometric amounts (Jin et al., 1997). It is possible that the relative inefficiency of the enzyme acting alone may contribute to the plateau levels of fragment formation observed in the coinfection experiments (FIGS. 2 and 3).

The fact that the HO site located at two positions in the adenovirus genome can be cleaved by HO endonuclease shows that the viral DNA is accessible to "foreign" enzymatic activity, at least at some stage in the replicative cycle. However, it is not known whether there is any stage specificity to cleavage at specific sites or any requirement for viral "chromosome" modification prior to cleavage. The data in FIG. 6 show that it is not necessary to enter the late phase of replication for the HO site located in E1 to be cleaved, but in an infection in which the Ad E1::HO gene virus was added to nonpermissive A549 cells 24 hour prior to the addition of the Ad E3::HO site virus, we were not able to detect any cleavage of the E3::HO site until the second virus had been resident for a further 8 hour (FIG. 3). Assuming that the HO endonuclease had had time to accumulate to high levels, it is surprising that the incoming HO site genome was not immediately cleaved, unless uncoating of the second virus DNA is incomplete until several hours postinfection. An alternative explanation would be that the DNA is cleaved efficiently but that at early times it is also repaired very efficiently (see below).

The initial rationale for developing adenovirus vectors expressing the HO endonuclease or containing the HO site was to follow the repair of DSBs created in vivo. Thus initially it was disappointing to discover no evidence for end-joining in the Ad E3::HO site by Ad E3::HO gene coinfection (FIG. 5). There are several possibilities for this apparent lack of end-joining. One is that the ends of the cleaved fragments are not accessible to the repair machinery, perhaps because the HO enzyme remains bound to the ends or because a significant proportion of the DNA is packaged. Evidence was obtained that the latter can occur (FIG. 4), but for reasons described below, we do not believe that this is necessary or sufficient to explain the lack of end-joined products. Another alternative is that the repair mechanism is so efficient that as soon as the HO endonuclease cleaves its site, creating two nicks in the DNA duplex held together by four complementary base pairs, the two nicks are resealed by DNA ligase. This would explain the lack of modified HO sites observed in the PCR analysis of the viral DNA pools obtained from the mixed infections and the failure to observe any trans products (FIG. 5). Again, we now believe that this idea is insufficient to explain the absence of end-joined products. A third and much more interesting possibility is that virus infection inhibits the end-joining mechanism of DSB repair.

The first evidence that viral gene products might inhibit end-joining came from a comparison of the coinfections with the Ad E1::HO viruses in either permissive 293 or nonpermissive A549 cells (FIG. 6). In the latter, the HO site is indeed cleaved but a new species of double the size of the end fragment is observed. Restriction endonuclease digestions showed conclusively that this is an inverted dimer of the end fragment, consistent with joining at the cleaved ends. This species was absent in coinfections in permissive 293 cells (FIG. 6) and very much reduced in coinfections of A549 cells with the Ads E1::HO site and Ads E3::HO gene viruses, in which E1 gene products are expressed. These results suggest that the appearance of the dimer species is inversely correlated with the expression of E1 gene products. Because E1A is required for the activation of all adenovirus early and late genes, the absence of one or more of their products could account for the apparent lack of inhibition of end-joining in A549 cells under conditions in which E1A is not expressed. Among the candidates for the gene products responsible for inhibition of end-joining are those of E4 region ORF3 and ORF6, whose absence leads to the formation of concatemers of adenovirus genomes in nonpermissive cells (Weiden and Ginsberg, 1994). The results with E3::HO vector viruses in which the whole of the E4 region has been deleted are consistent with this idea. In contrast to the results with the parental E3::HO viruses (FIGS. 5 and 7), cleavage of the E3 HO site is accompanied by the formation of dimer-sized molecules in nonpermissive A549 cells (FIG. 7). In contrast, the dimer-sized molecules were not observed in W162 cells (FIG. 7), in which E4 gene products are expressed from integrated sequences after E1A induction (Weinberg and Ketner, 1983). Thus the absence of E4 expression is correlated with the lack of inhibition of end-joining. The two E4 products most likely to contribute to this inhibition are the ORF6 protein (pORF6), which has been shown to interact with p53 (Dobner et al., 1996; Nevels et al., 1997), and pORF3, which is functionally redundant with pORF6 in the inhibition of genome concatemer formation (Weiden and Ginsberg, 1994) as well as some (Bridge and Ketner, 1989; Huang and Hearing, 1989) but not all other functions [for a recent example see Leppard and Everett (1999)]. Recently we constructed a virus that expresses pORF6 from the E1 region in an Ads E3::HO site E4 background. In triple infections of A549 cells with this virus, and the E3::HO site E4 and E3::HO gene E4 viruses, production of the dimer-sized species is markedly inhibited, suggesting that pORF6 can inhibit end-joining in the absence of all other E4 products. Consistent with this idea, recent data from Ketner and colleagues indicate that expression of pORF6 can inhibit VDJ joining in transient transfection assays (Boyer et al., 1999).

Why should the virus devote valuable genetic "space" to interfering with a fundamental cellular mechanism? The answer to this question may have two parts. First, the viral genome probably has little need for suuch mechanisms. The target size of the genome is small, its mode of DNA replication is distinct from that of the host with no need for precise coordination of leading and lagging strand synthesis, which may be a source of DSBs in the host cell genome, and it makes thousands of copies of its genome, which are randomly packaged into capsids. A rare DSB would not compromise the outcome of the infection. Second, genome concatemer formation must be avoided at late times in infection because adenovirus does not have a method of packaging unit length genomes from such concatemers. Although the 5' ends of adenovirus DNA are attached to the terminal protein, this is not a perfect protection from joining of termini, as Graham and colleagues first showed (Ruben et al., 1983; Graham, 1984) and the evidence of Weiden and Ginsberg (1994) confirmed. In this context, it is interesting that E4 products including ORF3 and ORF6 continue to be synthesized into the late phase of the infectious cycle (Dix and Leppard, 1993).

It may prove to be rewarding to try to identify the targets of the E4 products that inhibit DSBR. Recent evidence (Boyer et al., 1999) shows that pORF6 bind to the DNA-dependent protein kinase known to be involved in the control of the end-joining mechanism of FDBR (Finnie et al., 1996; Lieber et al., 1997; Jeggo, 1997), consistent with the observation mentioned above that expression of pORF6 can inhibit VDJ joining in transient transfection assays (Boyer et al., 1999).

Materials and Methods

Host Cells and Culture Methods

Human embryo kidney-derived 293 cells (Graham et al., 1977), which contain and express the adenovirus E1 region, were grown in monolayer culture in DMEM with 10% FetalClone II (Hyclone, Logan, Utah). These cells were used in tansfections to create E1-deleted vector viruses and in propagation and titration. Human A549 cells derived from a small cell carcinoma of the lung (Giard et al., 1973) were also grown in monolayer culture in DMEM with 10% supplemental calf serum (Hyclone). They were used in the creation, propagation, and titration of the E3-modified vector viruses. Monkey W162 cells (Weinberg and Ketner, 1983) which contain the adenovirus E4 region under E4 promoter control, were grown in monolayer culture in DMEM with 10% supplemental calf serum. They were used in the creation, propagation, and titration of the E3-modified, E4-deleted virus vectors.

The Construction of Adenovirus Vectors

Figure 1A:
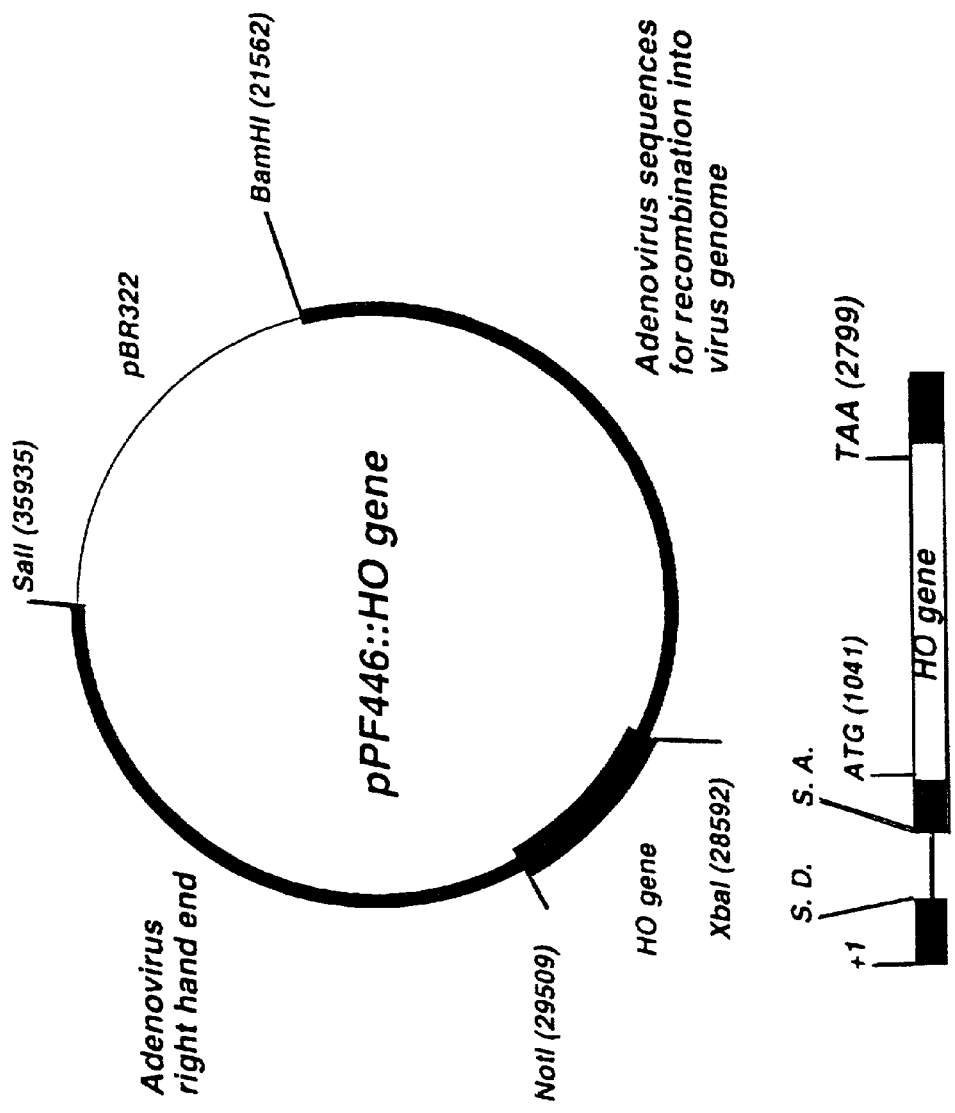
FIGS. 1A–1D Shuttle vectors for the construction of virus genomes containing the yeast HO endonuclease gene or the HO recognition site.
Figure 1B:
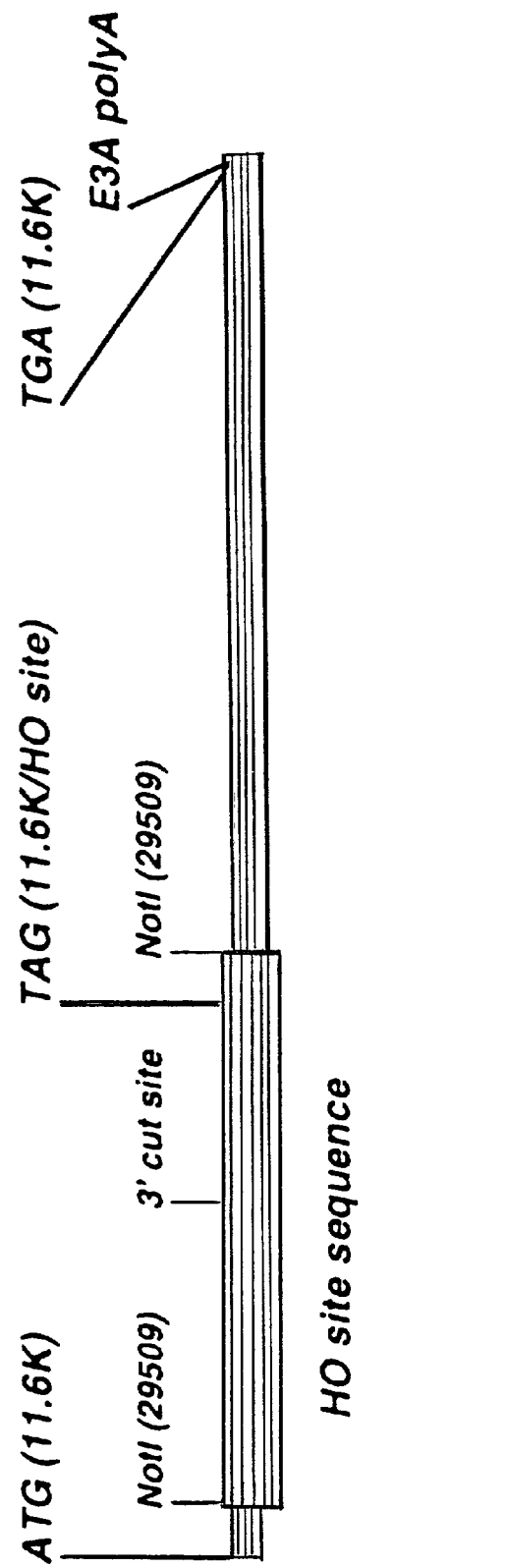

Vectors with insertions in the E3 region. The yeast HO endonuclease gene or the HO recognition site DNA were inserted into plasmid pPF446. This plasmid, constructed by Dr. Paul Freimuth, contains the right-hand end of the adenovirus serotype 5 genome extending from the BamHI site at bp 21,562 (Chroboczek et al., 1992) to a Sa/I linker added to the end of the ITR, cloned into the same restriction sites in pBR322. The HO gene sequence, flanked by unique XbaI and NotI sites and consisting of the ORF, 3 nt 5' of the initiator ATG and 54 nt 3' of the stop codon TAA (Russell et al., 1986), was obtained in a series of subcloning steps from plasmid pHOT, generously provided by the laboratory of Dr. Rodney Rothstein. The XbaI and NotI sites were used to replace the E3 sequence extending from the distal XbaI site at bp 28,592 to the NotI site at bp 29,509 (FIG. 1A). In this design, the initial transcript, containing the HO sequences, should be processed at the natural E3 splice sites and polyadenylation signals used in the formation of the abundant viral E3A mRNA "a" (Wold and Gooding, 1991). Sequences corresponding to the carboxy terminus of the E3A 6.7K gene, all of the E3A gp19K gene, and the amino terminus of the E3A 11.6K gene are deleted, while E3B sequences remain intact. The expected structure of the HO gene mRNA and ORF are shown in the lower part of FIG. 1A. A similar strategy was used to construct a derivative of pPF446 containing the HO site from the MATa locus. Plasmid pWJ421, also obtained from Dr. Rothstein's laboratory, was modified so that 117 bp of the HO site sequence was flanked by several polylinker sites including two NotI sites, giving a NotI fragment of 181 bp. The HO site sequence was cloned into the unique NotI site of pPF446, in the orientation opposite to that conventionally shown (Strathern, 1988). This insertion should disrupt the E3A 11.6K gene only, which may be translated as a hybrid protein with 10 amino acids of the original followed by 51 novel amino acids derived from the insertion (see FIG. 1B). Transfections were performed with each of the pPF446 derivatives and EcoRI-cut DNA-protein complex (DNA-PC) from LLX1 (Brunet et al., 1987), by standard procedures (Volkert and Young, 1983; Young et al., 1999), and recombinant viruses were isolated and analyzed to ensure that the correct genome structure had been created. Sequence analyses of the recombinant viruses confirmed the presence and expected sequences for the HO gene and site. The viral vectors, designated the Ad E3::HO gene and Ad E3::HO site, replicate to wild-type levels in human A549 cells.

A second pair of viruses was constructed in which the E4 deletion from H5dI366 (Halbert et al., 1986) was combined with the Ads E3::HO gene or site. This deletion is null for E4 expression. Ads E3::HO site E4 was constructed in a three-part overlap reaction as follows: DNA-PCs isolated from H5dI366 or from a phenotypically wild-type virus P54 (Munz et al., 1983) were cleaved with NdeI or EcoRI, respectively, and plasmid DNA from the pPF446::HO site was cleaved with BstEII. These cleavage reactions create a left-side overlap between the plasmid BstEII site at bp 24,843 and the P54 EcoRI site at bp 27,331 and a right-side overlap between the H5dI66 NdeI site at bp 31,048 and the plasmid BstEII site at bp 35,233. The cleaved DNA products were transfected into the E4 expressing W162 cells (Weinberg and Ketner, 1983) and viable virus was isolated from a "liquid yield" using techniques described in a detail previously (Volkert et al., 1989). Following a plaque assay on W162 cells, individual isolates were screened for the inability to replicate on A549 cells. Attempts to construct the AdS E3::HO gene E4 virus by similar means failed, so it was constructed as follows: The rightmost adenovirus SmaI fragment [the same fragment deleted in H5dI366 (Halbert et al., 1986)] was removed from the pPF446::HO gene in two steps: the NotI-SalI fragment was removed, and the deleted NotI to SalI fragment was replaced in the pPF446::HO gene. The resulting plasmid was used in an overlap reaction with DNA-PC from H5dI366 cleaved with EcoRI, SpeI, and SrfI and virus was screened for the appropriate genome structure, as described above for the HO site virus. As expected, both E4-deletion derivatives produced infectious virus in W162 cells, but not in A549 cells.

Figure 1C:
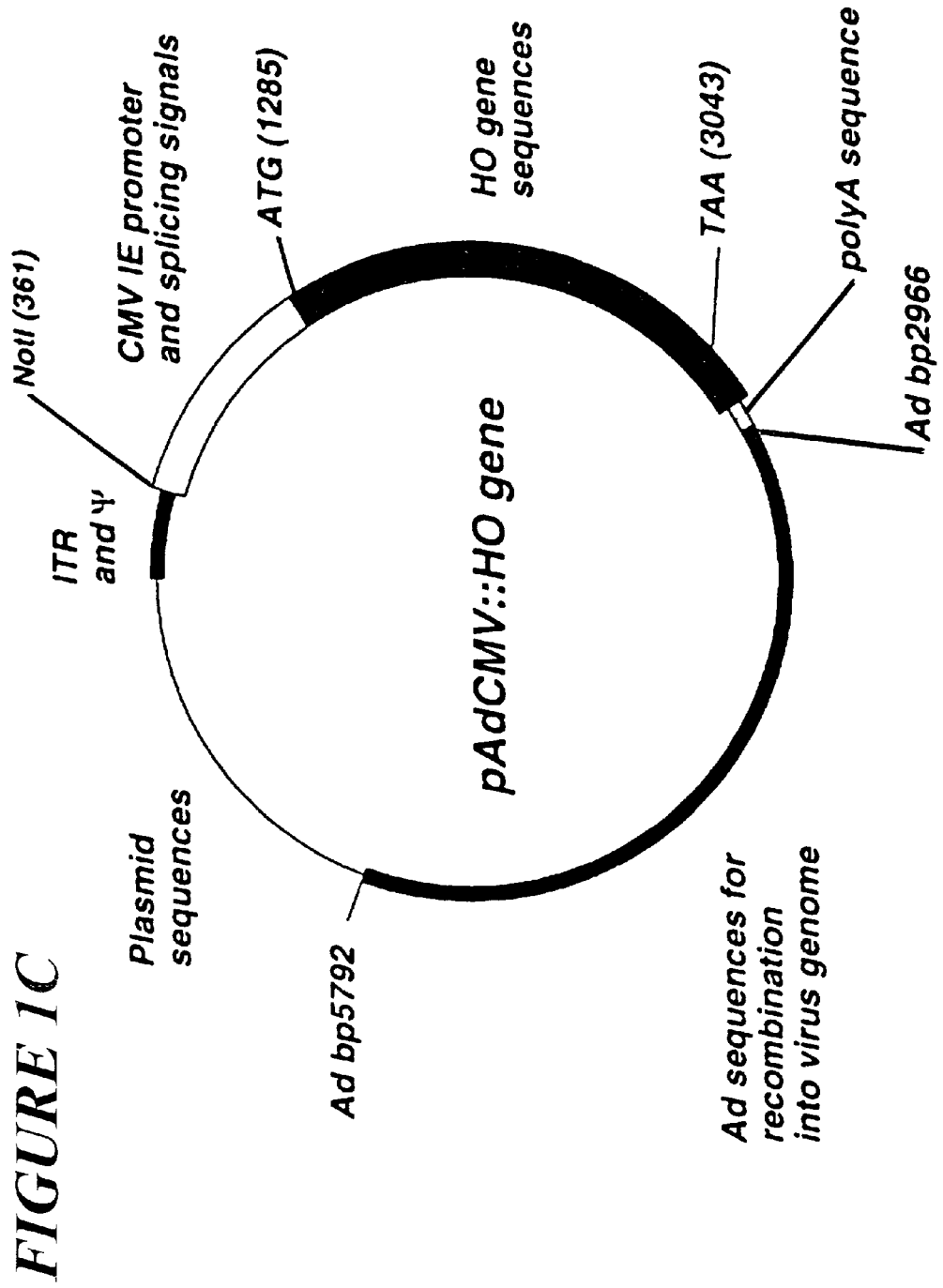
Figure 1D:
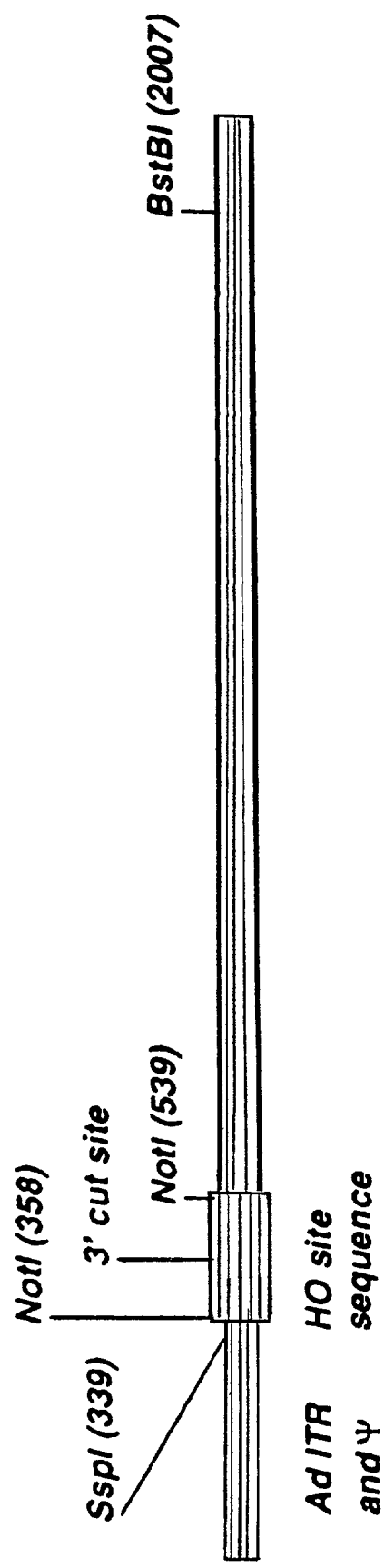

Vectors with insertions in the E1 region. Two different strategies were used to create the Ad E1::HO gene and Ad E1::HO site vectors. The yeast HO gene sequence described above was modified to have unique flanking HindIII and SalI sites, and these were cloned into pAdCMV (Falck-Pedersen et al., 1994), a modified form of pBR322 that contains the following elements clockwise from the EcoRI site: The left-hand ITR and the packaging sequence up to bp 355; the CMV immediate-early promoter and enhancer (Akrigg et al., 1985); sequences corresponding to artificial splice signals upstream of the cloning sites; the HindIII and SalI cloning sites; a poly(A) site selection sequence from the mouse β-globin major gene (Konkel et al., 1978); and finally adenovirus type 5 sequences from bp 2966 through 5792. The resulting plasmid pAdCMV::HO gene is shown in FIG. 1C. The virus Ad E1::HO gene was constructed by cotransfection, into early passage human 293 cells (Graham et al. 1977), of DNA from the pAdCMV::HO gene and from the larger than genome-sized plasmid pJM17, a kind gift of Dr. Frank Graham. Recombination between the DNAs of the HO gene-containing plasmid and pJM17 was expected to yield a genome within the packaging limit, whereas genomes derived from pJM17 itself are too large to package (McGrory et al., 1988). Virus arising from the yield was of the desired genome structure, and high-titer stocks were prepared from plaque-purified material. The virus Ad E1:: HO site was constructed using a different plasmid vector, pAdCMVcatgDneo$^+$ (Gall et al., 1996). This contains adenovirus sequences from the left-hand end as described for pAdCMV above and from bp 1575 to 5792. The adenovirus sequences flank a pair of mammalian expression cassettes controlling the neo and cat genes. The HO site sequence was cloned into a unique NotI site at bp 355 (FIG. 1D), using the fragment from pWJ421 described above. The orientation of the HO site is opposite to that of the site in E3. Virus was constructed by overlap recombination between the E1::HO site plasmid and XbaI-restricted DNA from an adenovirus genome containing a major deletion in E3 (Gall et al., 1996) and several XbaI sites at the left-hand end, to facilitate the exclusion of nonrecombinant genomes in the plaques resulting from the transfection on 293 cells. Both of the E1 vectors are replication-deficient on cell lines that do not express adenovirus E1A and thus must be propagated and titrated on 293 cells.

Viral Infections and Isolation of Intracellular Viral DNA

Human A549 or 293 cells and monkey W162 cells were grown in 35-mm dishes until confluent. The monolayers were infected at a multiplicity of either 5 or 10 fluorescent focus units per cell and incubated for various times, and the intracellular viral DNA was isolated by a modification of the Hirt (1967) technique, generally omitting the phenol separation step.

Analysis of Intracellular DNA by Southern Transfer-Hybridization

Intracellular DNA was isolated as described above and subjected to restriction enzyme digestion appropriate to the specific vector viruses used in the infection. The DNA fragments were resolved by agarose gel electrophoresis and transferred to nitrocellulose membranes (Protran; Schleicher and Schuell, Keene, N.H.) using methods described previously (Reach et al., 1990) Probes specific for different regions of the adenovirus genome (described in the appropriate figure legends) were prepared from whole plasmid DNA preparations by the random priming method (Feinberg and Vogelstein, 1983). Hybridization and washing conditions have been described previously (Reach et al., 1990). Quantitation of the amounts of parental genome DNA and of the DNA cleaved by HO endonuclease was performed on a PhosphorImager (Molecular Dynamics) using ImageQuant software.

PCR Analysis of Viral Genomes Containing the HO Site in Region E3

PCR was used to analyze intracellular viral DNA from A549 cells coinfected with Ad E3::HO site and Ad E3::HO gene viruses. Ten parallel infections were set up, DNA was isolated from 9 samples, while virus was harvested from the 10$^{th}$ infection and then used to inoculate another monolayer. One microliter of DNA from each of these 10 pools was subjected to PCR amplification with a Perkin-Elmer PCR kit. The reaction conditions were as follows: 1 mM HO primer II (5'-CCCACCCTAACAGAGATGACC-3') (SEQ ID NO:1), 1 mM HO primer III (5'-GCGGCCGCAATTC-CCGGGG-3') (SEQ ID NO:2), 2 mM MgCl$_2$, standard dNTP concentrations, and Taq polymerase and buffer concentrations. A Perkin-Elmer PCR thermocycler was used under the following conditions: 94° C. for 4 min, then 30 cycles of 94° C. for 1 min, 55° C. for 2 min, 72° C. for 3 min, 72° C. for 7 min. Five microliters of the reaction was analyzed by electrophoresis and a uniformly sized product of 220 bp was observed. The product was cloned using the TA cloning kit (Invitrogen), following the manufacturer's instructions. Individual colonies arising from the transformation were inoculated into 5 ml of LB with 50 µg/ml of kanamycin and grown overnight. DNA was prepared for sequencing using the "Speedprep" method (Goode and Feinstein, 1992), one-half of the final yield of DNA was denatured, and T7 or SP6 primer was annealed. Sequencing was performed using the "Sequenase" kit (U.S. Biochemical) with dGTP termination solutions, according to the manufacturer's instructions.

Construction of Virus E1::ORF6 (VORF6)

The construction method is illustrated in FIG. 9. Human 293 cells were transfected with DNA isolated from virus E3::HO site delta E4 (a derivative of dl366). This genome contains a major deletion in E4 and lacks the coding capacity for any of the E4 proteins. The E3::HO site modification was used for specific purposes to do with the analysis of double strand break repair and is irrelevant for the design of the vector. Cells transfected with the full length genome alone did not yield infectious virus because of the absolute requirement for at least one or the other of the E4 proteins ORF6 or ORF3 for a complete replicative cycle. One set of cells was co-transfected with a shuttle vector plasmid (Young et al., 1999) containing the cDNA for ORF6 under the control of the CMV immediate early promoter. This expression cassette replaces the E1 region and is flanked by adenovirus sequences. Recombination in these flanking regions present in the full length genomic DNA and the plasmid was expected to yield a genome capable of replication in 293 cells because ORF6 expression from the virus and E1 expression from the 293 cell allow a full replication cycle to proceed. As expected, the co-transfection yielded infectious virus. Virus was plaque-purified and characterized further to ensure that the genomic structure was as predicted, and that ORF6 was indeed expressed.

REFERENCES

Akrigg, A., Wilkinson, G. W. G., and Oram, J. D. (1985). The structure of the major immediate early gene of human cytomegalovirus strain AD 169. *Virus Res.* 2, 107–121.

Anton, M., and Graham, F. L. (1995). Site-specific recombination mediated by an adenovirus vector expressing the Cre recombinase protein: A molecular switch for control of gene expression. *J. Virol.* 69, 4600–4606.

Baumann, P., and West, S. C. (1998). DNA end-joining catalyzed by human cell-free extracts. *Proc. Natl. Acad. Sci. USA* 95, 14066–14070.

Berkner, K. L. (1988). Development of adenovirus vectors for the expression of heterologous genes. *Biotechniques* 6, 616–629.

Boyer, J., Rohleder, K., and Ketner, G. (1999). Adenovirus E4 34k and E4 ilk inhibit double strand break repair an dare physically associated with the cellular DNA-dependent protein kinase. *Virology* 263, 307–312.

Bridge, E., and Ketner, G (1989). Redundant control of adenovirus late gene expression by early region 4. *J. Virol.* 63, 631–638.

Brunet, L. J., Babiss, L. E., oung, C. S. H., and Milld, D. R. (1987). Mutation in the adenovirus major late pomoter: Effects upon viability and transcriprion during infection. *Mol. Cell. Biol* 7, 1091–1100.

Chee-Sheung, C. C., and Ginsberg, H. S. (1982). Characterization of temperature-sensitive fiber mutant of type 5 adenovrus and effect of the mutation on virion assembly. *J. Virol.* 42, 932–950.

Chiurazzi, M., Ray, A., Viret J. F., Perera, R., Wang, X. H., Lloyd, A. M., and Signer, E. R. (1996). Enhancement of somatic intrachromosomal homoloous recombination in *Arabidopsis* by the HO endonuclease. *Plant Cell* 8, 2057–2066.

Choulika, A. Perrink A, Dujon, B., and Nicolas, J.-F (1995). Induction of homologous recombination in mammalian chromosomes by using the I-Scell system of *Scaccharomyces cerecisia*. *Mol. Cell. Biol*, 15, 1968–1973.

Chroboczek, J., Bieber, F., and Jacrot, Be. (1992). The sequence of the genome of adenovirus type5 and its comparison with the genome of adenovirus type 2. *Virology* 186, 280–285.

Cladaras, C., and Wold, W. S. M. (1985). DNA sequence of the early E3 transcription unit of adenovirus 5. *Virology* 140, 28–43.

Colicos, M. A., Haj-Ahmad, Y., Valerie, K. Henderson, E. E., and Rainbow, A. J. (1991). Construction of a recombinant adenovirus containing the denV gene bacteriophage T4 which can partially restore the DNA repair deficiency in xeroderma pigmentosum fibroblasts. *Carcinogenesis* 12, 249–255.

Costa, N. D., and Bryant, P. E. (1991). Elevated levels of DNA double-strand breaks (dsb) in restriction endonuclease-treated xrs5 cells correlate with the reduced capacity to repair dsb. *Mutat. Res. DNA Repair* 255, 219–226.

Dix, I., an d Leppard, K. N. (1993). Regulated splicing of adenovirus type 5 E4 transcripts and regulated cytoplasmic accumulation of E4 mRNA. *J. Virol.* 67, 3226–3231.

Dobbelstein, M., Roth, J., Kimberly, W. T., Levine, A. J., and Shenk, T. (1997). Nuclear export of the E1B 55-kDa and E4 34-kDa adenoviral oncoproteins mediaed by a rev-like signal sequence. *EMBO J.* 16, 4276–4284.

Dobner, T., Horikoshi, N., Rubenwolf, S., and Shenk T. (1996). Blockage by adenovirus E4orf6 of transcriptional activation by the p53 tumor suppressor. *Science* 272, 1470–1473.

Dronkert, M. L. G., Beverloo, H. B., Johnson, R. D., Hoeijmakers, J. H. J., Jasin, M., and Kanaar, R. (2000). Mouse RAD54 affects DNA double-strand break repair and sister chromatid exchange. *Mol. Cell. Biol.* 20, 3147–3156.

Eck, S. L., Alavi, J. B., Judy, K., Phillips, P., Alavi, A., Hackney, D., Cross, P., Hughes, J., Gao, G. P., Wilson, J. M., and Propert, K. (2001). Treatment of recurrent or progressive malignant glioma with a recombinant adenovirus expressing human interferon-beta (H5.010CMVhIFN-b): A phase I trial. *Hum. Gene Ther.* 12, 97–113.

Elliot, B., Richardson, C., Winderbaum, J., Nickoloff, J. A., and Jasin, M. (1998). Gene conversion tracts from double-strand break repair in mammalian cells. *Mol. Cel. Biol.* 18, 93–101.

Falk-Pedersen, E., Heinflink, M., Alvira, M., Nussenzveig, D. R., and Gershengorn, M. C. (1994). Expression of thyrotropin-releasing hormone reeptors by adenovirus-mediated gene transfer reveals that thyrotropin-releasing hormone desensitization is cell specific. *Mol. Pharmacol.* 45, 684–689.

Feinberg, A. P., and Voelsten, B. (1983). A technique for readiolabeling DNA restriction endonuclease fragments to high specific activity. *Anal. Diochem.* 132, 6–13.

Finnie, N. J., Gottlieb, T. M., Blunt, T., Jeggo, P. A., and Jackson, S. P. (1996). DNA-dependent protein kinase defects are linked to deficiencies in DNA repair and V(D)J recombination. *Philos. Trans. R. Soc. London Biol.* 351, 173–179.

Gall, J., Kass-Eisler, A., Leinwand, L., and Falck-Pedersen, E. (1996). Adenovirus type 5 and 7 capsid chimera: Fiber replacement alters receptor tropism without affecting primary immune neutralization epitopes. *J. Virol.* 70, 2116–2123.

Giard, D. J., Aaronson, S. A., Todaro, G. J., Arnstein, P., Kersey, J. H., Dosik, H., and Parks, W. P. (1973). In vitro cultivation of human tumors: Establishment of cell lines derived from a series of solid tumors. *J. Natl. Cancer Inst.* 51, 1417–1423.

Gluzman, Y., Teichl, H., and Solnick, D. (1982). Helper-free adenovirus type 5 vectors. In "Eukaryotic Viral Vectors" (Y. Gluzman Ed.), pp. 187–192. Cold Spring Harbor Laboratory Press, Cold Spring harbor, N.Y.

Goode, B. L., and Feinstein, S. C. (1992) "Speedprep" purification of template for double-stranded DNA sequencing. *Biotechniques* 12, 148–149.

Gräble, M., and Hearing, P. (1992). cis and trans requirements for the selective packaging of adenovirus type 5 DNA. *J. Virol.* 66, 723–731.

Graham, F. L., (1984). Covalently closed circles of human adenovirus are infectious. *EMBO J.* 3, 2917–2922.

Graham, F. L., Smiley, J., Russell, W. C., and Nairn, R. (1977). Characteristics of a human cell line transforms by DNA from human adenovirus type 5. *J. Gen. Virol.* 36, 59–72.

Haber, J. E. (1995). In vivo biochemistry: Physical monitoring of recombination induced by site-specific endonucleases. *BioEssays* 17, 609–620.

Halbert, D. N., Cutt, J. R., and Shenk, T. (1986). Adenovirus early region 4 encodes functions required for efficient DNA replication, late gene exression, and host cell shutoff. *J. Virol.* 56, 250–257.

Hammarskjöld, M,-L, and Winberg, G. (1980). Encapsidation of adenovirus 16 DNA is directed by a small DNA sequence at the left end of the genome. *Cell* 20, 787–795.

Hardy, S., Kitamura, M., Harris-Stansil, T., Dai, Y., and Phipps, M. L. (1997). Construction of adenovirus vectors through cre-lox recombination. *J. Virol.* 71, 1842–1849.

Hirt, B. (1967). Selective extraction of polyoma DNA from infected mouse cells cultures. *J. Mol. Biol.* 26, 365–169.

Huang, M.-M., and Hearing, p. (1989). Adenovirus early region 4 encodes two gene products with redundant effects in lytic infection. *J. Virol.* 63, 2605–2615.

Jeggo, P. A. (1997). DNA-PK: At the cross-roads of biochemistry and genetics. *Mutat. Res. DNA Repair* 384, 1–14.

Jeggo, P. A. (1998). Identification of genes involved in repair of DNA double-strand breaks in mammalian cells. *Radiat. Res.* 150 (Suppl.), S80–S91.

Jin, Y., Binkowski, G., and Norris, D. (1997). Ho endonuclease cleaves MAT DNA in vitro by an inefficient stoichiometric reaction mechanism. *J. Biol. Chem.* 272, 7352–7359.

Johnson, R. D. and Jasin, M. (2000). Sister chromatid gene conversion is a prominent double-strand break repair pathway in mammalian cells. *EMBO J.* 19, 3398–3407.

Kanaar, R., Hoeijmakers, J. H. J, and Van Gent, D. C. (1998). Molecular mechanisms of DNA double-strand break repair. *Trends Cell Biol.* 8, 483–489.

Kanegae, Y., Lee, G., Sato, Y., Tanaka, M., Nakai, M., Sakaki, T., Sugano, S., and Saito, I. (1995). Efficient gene activation in mammalian cells by using recombinant adenovirus expressing site-specific Cre recombinase. *Nucleic Acids Res.* 23, 3816–3821.

Khuri, F. R., Nemunaitis, J., Ganly, I., Arseneau, J., Tannock, I. F., Romel, L., Gore, M., Ironside, J., MacDougall, R. H., Heise, C., Randlev, B., Gillenwater, A. M., Bruso, P., Kaye, S. B., Hong, W. K., and Kirn, D. H. (2000). A controlled trial of intratumoral ONYX-015, a selectively-replicating adenovirus, in combination with cisplatin and 5-fluorouracil in patients with recurrent head and neck cancer. *Nature Med.* 6, 879–885.

Klessig, D. F. (1984). Adenovirus-simian virus 40 interactions. In "The Adenoviruses" (H. S. Ginsberg, k Ed.), pp. 399–449. Plenum, N.Y.

Konkel, D. A., Tilghman, S. M., and Leder, P. (1978). The sequence of the chromosomal moiuse b-globin major gene: homologies in capping, splicing and poly(A) sites. *Cell* 15, 1125–1132.

Leppard, K. N., and Everett, R. D. (1999). The adenovirus type 5 E1b 55K and E4 Orf3 protiens associate in infected cells an daffect ND10 components. *J. Gen. Virol.* 80, 997–1008.

Lewis, L. K., Kirchner, J. M., and Resnick, M. A. (1999). Requirement for end-joining and checkpoint functions, but not RAD52-mediated recombination, after EcoRI endonuclease cleavage of *Saccharomnyces cerevisiae*: DNA. *Mol. Cell. Biol.* 18, 1891–1902.

Lewis, L. K., Westmoreland, J. W., and Resnick, M. A. (1999). Repair of endonuclease-induced double-strand breaks in *Saccharomyces cerceisiae*: Essential role gor genes associated with nonhomoloogous end-joining. *Genetice* 152, 1513–1529.

Liang, F. Romanienko, P. J., Weaver, D. T., Jeggo, P. A., and Jasin, M. (1996). Chromosomal double-strand break repair in Ku80-deficient cells. *Proc. Natl. Acad. Sci. USA* 93, 8929–8933.

Lieber, M. R. (1998). Pathological and pusiological double-strand breaks-Roles in cancer, aging, and the immune system. *AM. J. Pathol.* 153, 1323*1332.

Lieber, M. R., Grawunder, U., Wu, X. T., and Yaneva, M. (1997). Tying loose ends: Roles of Ku and DNA dependent protein kinase in he repair of doubl-strand breaks. *Curr. Opin. Genet. Dev.* 7, 99–104.

Liu, N., and Bryant, P. E. (1993). Response of ataxia telangiectasia cells to restriction endonuclease induced DNA double-strand breaks. I. Cytogenetic characterization. *Mutagenesis* 8, 503–510.

Mautner, V., and Mackay, N. (1984). Recombination in adenovirus: Analysis of crossover sites in intertypic overlap recombinants. *Virology* 139, 43–52.

McGrory, W. J., Bautista, D. S., and Graham, F. L. (1988). A simple technique for the rescue of early region 1 mutations into infectious human adenovirus type 5. *Virology* 163, 614–617.

Moynahan, M. E., and Jasin, M. (1997). Loss of heterozygosity induced by a chromosomal double-strand break. *Proc. Natl. Acad. Sci. USA* 94, 8988–8993.

Munz, P. L., young, C., and Young, C. S. H. (1983). The genetic analysis of adenovirus recombination in triparental and superinfection crosses. *Virology* 126, 576–586.

Nemunaitis, J., Ganly, I., Khuri, F., Arseneau, J., Kuhn, J., McCarty, T., Landers, S., Maples, P., Romel, L., Randlev, B., Reid, T., Kaye, S., and Kirn, D. (2000). Selective replication and oncolysis in p53 mutant tumors with ONYX-015, an E1B-55kD gene-deleted adenovirus, in patients with advanced head and neck cancer: A Phase II trial. *Cancer Res.* 60, 6359–6366.

Nemunaitis, J., Khuri, F., Ganly, I., Arseneau, J., Posner, M., Vokes, E., Kuhn, J., McCarty, T., Landers, S., Blackburn, A., Romel, L., Randlev, B., Kaye, S., and Kirn, D. (2001). Phase II trial of intratumoral administration of ONYX-015, a replication-selective adenovirus, in patients with refractory head and neck cancer. *J. Clin. Oncol.* 19, 289–298.

Nevels, M., Rubenwolf, S., Spruss, T., Wolf, H., and Dobner, T. (1997). The adenovirus E4orf6 protein can promote E1A/E1B-induced focus formation by interfering with p53 tumor suppressor function. *Proc. Natl. Acad. Sci. USA* 94, 1206–1211.

Parks, R. J., Chen, L., Anton, M., Sankar, U., Rudnicki, M. A., and Graham, F. L. (1996). A helper-dependent adenovirus vector system: Removal of helper virus by Cre-mediated excision of the viral packaging signal. *Proc. Natl. Acad. Sci. USA* 93, 13565–13570.

Phillips, J. W., and Morgan, W. F. (1994). Illegitimate recombination induced by DNA double-strand breaks in a mammalian chromosome. *Mol. Cell. Biol.* 14, 5794–5803.

Reach, M., Babiss, L. E., and Young, C. S. H. (1990). The upstream factor binding site is not essential for activation of transcription from the adenovirus major late promoter. *J. Virol.* 64, 5851–5860.

Richardson, C., Moynahan, M. E., and Jasin, M (1998). Double-strand break rpair by interchromosomal recombination: Suppression of chromosomal translocations. *Genes. Dev.* 12, 3831–3842.

Rolig, R. L., Layher S. K., Santi, B., Adair, G. M., Gu, F., Rainbow, A. J., and Nairn, R. S. (1997). Survival, mutagenesis, and host cell reactivation in a Chinese hamster ovary cell ERCC1 knock-out mutant. *Mutagenesis* 12, 277–283.

Roth, D., and Wilson, J. (1988). Illegitimate recombinatiomn in mammalian cells. In "Genetic Recombination" (Rl. Kucherlapati and G. R. Smith, Eds.), pp. 621–653. Am. Soc. Microbiol., Washington, D.C.

Rouet, p., Smih, F., and Jasin, M. (1994a). Introduction of double-strand breaks into the genome of mouse cell by expression of a rare-cutting endonuclease. *Mol. Cell. Biol.*, 14, 8096–8106.

Rouet, P., Smih, F., and Jasin, M. (1994b). Expression of a site-specific endonuclease stimulates homologous recombination in mammalian cells. *Proc. Natl. Acad. Sci. USA* 91, 6064–6068.

Ruben, M., Bacchetti, S., and Graham, F. (1983). Covalently closed circles of adenoviros 5 DNA. *Nature* 301, 172–174.

Rubenwolf, S. m Schütt, H., Nevels, M. Wolf, H., and Dobner T, (1997). Structural analysis of the adenobirus type 5 E1B 55-kilodalton-E4orf6 protein complex. *J. Virol.* 71, 1115–1123.

Russell, D. W., Jensen, R., Zoller, M. J., Burke, J., Errede, B., Smith M., and Herskowitz, I. (1986) Structure of the *Saccharomyces cerevisiae* HO gene and analysis of its upseam regulatory region, *Mol. Cell. Biol.* 6, 4281–4294.

Sargent, R. G., Brenneman, M. A., and ilson, J. H. (1997). Repair of site-specific double-strandb breaks in a mammalian chromosome by homologous and illegitimate recombination. *Mol. Cell. Biol.* 17, 267–277.

Sarnow, P., Hearing, P., Anderson, C. W., Halbert, D. N., Shenk, T., and Levine, A. J. (1984). Adenovirous early region 1B 58,000-dalton tumor antigen is physically associated with an early region 4 25,000-dalton protein in productively infected cells. *J. Virol.* 49, 692–700.

Schmid, S. I., and Hearing, P. (1997). Bipartite structure and functional independence of adenovirus type 5 packaging elements. *J. Virol.* 71, 3375–3384.

Schuler, M., Herrmann, R., De Greve, J. L. P., Stewart, A. K., Gatzemeier, U., Stewart, D. J., Laufman, L., Gralla, R., Kuball, J., Buhl, R., Heussel, C. P., Kommoss, F., Perruchoud, A. P., Shepherd, F. A., Fritz, M. A., Horowitz, J. A., Huber, C., and Rochlitz, C. (2001). Adenovirus-mediated wild-type p53 gene transfer in patients receiving chemotherapy for advanced non-small-cell lung cancer: Results of a multicenter phase II study. *J. Clin. Oncol.* 19, 1750–1758.

Strahern, J. N. (1988). Control and execution of homothallic switching in *sacharomyces cerevisiae*. In "Genetic Recombination" (R. Kucherlapati and G. R. Smith, Eds.), pp. 445–464. Am. Soc. Microbiol., Washington, DC.

Volkert, F. C., and Young, C. S. H. (1983). The genetic analysis of recombination using adneovirus overlapping terminal DNA fragments. *Virology* 125, 175–193.

Volkert, F. C., Munz, P. L., and Young, C. S. H. (1989). A genetic investigation of the mechanism of adenovirus marker rescue. *Virology* 173, 77–88.

Wang, P., Anton, M., Graham, F. L., and Bacchetti, S. (1995). High frequency recombination between loxP sites in human chromosomes mediated by an adenovirus vector expressing Cre recombinase. *Somat. Cell. Mol. Genet.* 21, 429–441.

Wang, R., Jin, Y., and Norris, D. (1997). Identification of a protein that binds to the Ho endonuclease recognition sequence at the yeast mating type locus. *Mol. Cell. Biol.* 17, 770–777.

Wang, y., Kruchel, L. A., and Edelman, G. M. (1996). Targeted DNA recombination in vivo using an adenovirus carrying the cre recombinase gene. *Proc. Natl. Acad. Sci. USA* 93, 3932–3936.

Wang, H. C., Zeng, Z. C., Bui, T. A., Sonoda, E., Takata, M., Takeda, S., and Iliakis, G. (2001). Efficient rejoining of radiation-induced DNA double-strand breaks in vertebrate cells deficient in genes of the RAD52 epistasis group. *Oncogene* 20, 2212–2224.

Weiden, M. D., and Ginsberg, H. S. (1994) deletion of th eE4 region of the genome produces adenovirus DNA concatemers. Proc, Natl. Acad. Sci. USA 91, 153–157.

Weinberg, D. H., and Ketner, G. (1983). A cell line that supports the growth of a defective early region 4 deletion mutant of human adenovirus type 2. *Proc. Natl. Acad. Sci. USA* 80, 5383–5386.

Wold, W. S. M., and Gooing, L. R. (1991) Region E3 of adcenovirus: A cassette of genes involved in host immunosureveillance and virus-cell interations. *Virology* 184, 1–8.

Young, C. S. H., Nicholás, A. L., Lu, H., Lu, H., and Munz, P. L. (1999). Methods for creating and analyzing adenovirus vectors which express proteins that act on the viral genome. In "Methods in Molecular Medicine: Adenovirus Methods and Protocols" (W. S. M. Wold, Ed.), pp. 61–83. Humana Press, Totowa, N.J.

Zdzienicka, M. Z. (1999). Mammalian X-ray-sensitive mutants which are defective in non-homologous (illegitimate) DNA double-strand break repair. *Biochimie* 81, 107–116.

Experimental Details

Second Series

The adenovirus E4 11k and E4 34k proteins (the products of E4 ORFs 3 and 6) individually prevent the formation of concatemers of the linear adenoviral genome in infected cells (Weiden and Ginsberg, 1994). Genome concatenation does not occur in E4 mutant infections of a cell line (MO59J) that lacks the cellular DNA-dependent protein kinase (DNA PK), suggesting that concatemers arise by end-joining mediated by the DNA PK-dependent double strand break repair (DSBR) system. Consistent with this hypothesis, E4 34k also inhibits V(D)J recombination, a normal cellular process mediated by DSBR and dependent on DNA PK. Both E4 34k and E4 11k coimmunoprecipitate with DNA PK. Together, these observations indicate that E4 products block formation of concatemers of the viral genome by inhibiting double strand break repair, and suggest that they act by forming a physical complex with DNA PK.

The interaction of E4 products with DNA PK may increase the efficiency of viral infection in two ways. First, since neither viral DNA replication nor packaging are likely to utilize multimeric substrates effectively, preventing concatemer formation probably stimulates both processes. Second, the interaction may inhibit apoptosis of infected cells that might otherwise be induced specifically by the products of viral DNA replication. Both linear adenoviral DNA and partially single-stranded branched viral replication intermediates resemble damaged cellular DNA. Viral replication products present in infected cells therefore might be expected to activate the DNA damage-sensing system which, in turn, can induce apoptosis. DNA PK is required for activation of p53 DNA binding by DNA damage (Woo et al., 1998). By blocking DNA PK function, E4 products may prevent p53 activation mediated by the DNA damage-sensing system and thus help prevent apoptosis induced by that pathway.

E4 Products Inhibit Concatenation of the Adenoviral Genome by DSBR

To test the dependence of concatemer formation on DSBR, viral DNA in cells that lack DNA PK and therefore are defective for DSBR were examined. MO59J, a DNA PK⁻ human glioma cell line, and MO59K, a DNA PK⁺ cell line derived from the same tumor (Allalunis-Turner et al., 1993, Lees-Miller et al., 1995), were infected with adenovirus type 5 (Ad5) or the deletion mutant H5dl1011, which lacks all recognized E4 open reading frames (Bridge and Ketner, 1989). 52 h after infection, the infected cells were collected and the intracellular DNA analyzed by pulsed-field gel electrophoresis and Southern blotting (Van der Ploeg et al., 1984, Southern, 1975) (FIG. 10). In DNA PK$^{30}$ MO59K cells, the E4 mutant produced concatemeric molecules up to at least seven genomes in length, as do E4 mutants in infections of Hela cells. In contrast, the E4 mutant virus produced no detectable concatemeric DNA in DNA PK⁻ MO59J cells. Wild-type Ad5 produced exclusively monomeric viral DNA in both cell lines. Therefore, concatemer formation in E4 mutant infections occurs by a DNA PK-dependent process, consistent with the hypothesis that concatenation is the result of end-to-end joining of monomeric viral genomes by DSBR. These data also confirm that concatemer formation is suppressed by one or more E4 products.

Effects of E4 34k on V(D)J Recombination

If E4 products prevent concatenation of viral DNA by blocking DSBR they might also interfere with normal cellular processes that require DSBR. Among those is V(D)J recombination, a DNA rearrangement required for the assembly of functional immunoglobulin and immunoglobulin-related genes during development of the immune system. V(D)J recombination is initiated by the production of double-strand breaks at signal sequences within an immunoglobulin locus by a site-specific endonuclease consisting of the Rag1 and Rag2 proteins (McBlane et al., 1995). The cleaved DNA is then rejoined to produce an intact immunoglobulin gene (coding joint formation) and a circular molecule containing the excised signal sequences and intervening DNA (signal joint formation) (Jeggo, Taccioli, and Jackson, 1995). Formation of both the intact immunoglobulin gene and the circular, excised DNA segment requires components of the DSBR system, including DNA PK (Hesse et al., 1987, Shin, Perryman, and Meek, 1997). The effects of E4 11k and E4 34k on V(D)J recombination were tested in a transfection system where rearrangement of an immunoglobulin signal-bearing substrate plasmid can be quantified (Hesse et al., 1987). 293 cells were transfected with plasmids encoding Rag1 and Rag2 (Lin and Desiderio, 1993), a plasmid containing a substrate for V(D)J recombination (pJH200, which simulates signal joint formation (Hesse et al., 1987)), a plasmid encoding either E4 11k or E4 34k (or an empty vector control), and a plasmid encoding SV40 T antigen (which mediates plasmid amplification in transfected cells). 48h after transfection, plasmid DNA was recovered from the cells and introduced into *E. coli* by electroporation. The substrate plasmid carries a constitutively-expressed ampicillin-resistance gene and a chloramphenicol acetyl transferase (CAT) gene separated from its promoter by a segment of DNA that is flanked by V(D)J recombinational signals and that contains a transcriptional stop signal (Hesse et al., 1987). V(D)J recombination excises the DNA containing the stop signal, juxtaposing the CAT gene and its promoter. Recombined plasmids will express the CAT gene and confer chloramphenicol resistance after introduction into bacterial cells, and recombination frequency can be determined by measuring the fraction of all plasmids recovered from the transfected cells (which confer ampicillin resistance) that also confer resistance to chloramphenicol (recombinant plasmids only).

The presence of E4 34k reduced recombinant formation about five-fold, compared to cells transfected with an empty vector (FIG. 11A). The accumulation of Rag proteins was unaffected by E4 34k, as estimated by immunoblotting (FIG. 11B), indicating that E4 34k does not reduce recombination simply by preventing expression of the transfected rag genes. These data provide independent confirmation of the hypothesis that E4 34k interferes with DSBR. In addition, they demonstrate that E4 34k can act as an inhibitor of DSBR activity on substrates other than viral DNA and outside of the specialized conditions of a viral infection. In contrast to the behavior of E4 34k, E4 11k did not affect the frequency of V(D)J recombination even though E4 11k expression was comparable to that of E4 34k (FIG. 11B). It is possible that E4 11k inhibits an element of DSBR not required for signal joint formation in the transfection system; different joining reactions can require different proteins (Jeggo, Taccioli, and Jackson, 1995). Alternatively, E4 11k might interfere with the action of DSBR on viral DNA exclusively due to compartmentalization. E4 11k might also prevent accumulation of concatemers by promoting separation of concatenated molecules once concatemers are formed. In any event, E4 34k and E4 11k apparently act to inhibit adenovirus genomic concatenation by different mechanisms. E4 34k and E4 11k also participate in the regulation of viral late gene expression, where they are individually sufficient to stimulate the accumulation of viral late mRNAs. In that case also, despite the overall similarity of their activities, their mechanisms of action differ (Bridge and Ketner, 1990).

E4 34K Associates Physically with DNA Protein Kinase

Because DNA PK is essential for concatemer formation and for V(D)J recombination, interactions between E4 products and DNA PK might account for the inhibition of both processes by E4. Therefore, immunoprecipitation was used to search for evidence of physical associations between DNA PK and the E4 34k and E4 11k proteins. 293 cells were transfected with E4 expression plasmids and DNA PK, E4 34k, or E4 11k were immunoprecipitated using specific antisera. Precipitates were then examined for the other proteins by immunoblotting. Immunoprecipitates made from E4 34k-transfected cells with an anti-E4 34k polyclonal antibody (Boivin et al., 1999) (FIG. 12A) contained a protein of molecular weight >200 kDa that was reactive with antibodies against the catalytic subunit of DNA PK (DNA PK$_{cs}$; MW approx. 470 kDa (Hartley et al., 1995)). DNA PK$_{cs}$ was absent from identical immunoprecipitates made from cells that lack E4 34k, and therefore does not cross-react with the E4 34k serum used. Similarly, immunoprecipitates made from E4 34k-transfected cells with a monoclonal antibody directed against DNA PK$_{cs}$ (FIG. 12B) contained E4 34k, while immunoprecipitates made from cells transfected with an empty expression plasmid did not. E4 34k was not detected in immunoprecipitates made from transfected cell extracts with an irrelevant, isotype-matched monoclonal antibody (data not shown). These observations demonstrate that there is a physical interaction, direct or indirect, between E4 34k and DNA Pk$_{cs}$.

Immunoprecipitates made with DNA PK antibodies were examined also for E4 11k by immunoblotting using an E4 11k anti-peptide serum. Precipitates made from E4 11k-transfected cells with both polyclonal and monoclonal anti-DNA PK antibodies contained E4 11k (FIG. 12C). Small amounts of E4 11k are also present in precipitates made with preimmune serum (FIG. 12C), with an irrelevant isotype-matched monoclonal antibody and with resin alone. Nevertheless, specific DNA PK antibodies precipitate substantially more E4 11k than do the controls and we think it likely that E4 11k, like E4 34k, participates in a direct or indirect physical interaction with DNA PK.

The observation that E4 products both inhibit DSBR and interact physically with DNA PK suggested that E4 interferes with DSBR by binding to DNA PK and inhibiting its enzymatic activity. To address that possibility, DNA PK activity was measured by a peptide phosphorylation assay in nuclear extracts made from uninfected Hela cells and from Hela cells infected with Ad5 (E4$^+$) or with the E4 deletion mutant H5dl1007 (Bridge and Ketner, 1989). In two independent experiments, phosphorylation of the peptide by extracts from wild-type-, E4 mutant-, and mock-infected cells were not significantly different. Viral genome concatenation, assayed by PFGE analysis of DNA from a portion of the cells assayed for DNA PK activity, was completely inhibited in cells infected by wild-type virus but was comparable in H5dl1007-infected cells to that seen earlier with H5dl1011. Thus, at least as assessed by peptide phosphorylation in vitro, E4 does not affect DNA PK enzymatic activity in cells where it inhibits concatenation completely. It must be emphasized that this assay for DNA PK activity may not accurately reflect activity on critical protein substrates in vivo, or that E4 products might block DSBR by inhibiting aspects of DNA PK function not reflected by its protein kinase activity.

Extensive concatenation of intracellular viral DNA presumably would reduce the efficiency of an adenovirus infection. Viral origins of replication must be located near the end of a DNA molecule to be active in the in vitro DNA replication system (Rawlins et al., 1984), and concatenated viral genomes therefore may be poor substrates for replication in vivo. Similarly, the adenovirus packaging sequences do not function when located more than a few hundred base pairs from the genomic termini (Hearing et al., 1987), suggesting that concatemers would not be good packaging substrates. Circular viral DNA molecules are infectious (Graham, Rudy, and Brinkley, 1989), and mechanisms for the replication or resolution of viral DNA molecules with end-to-end joints therefore must exist. However, prevention of concatemer formation may be preferable to the resolution of concatemers after they are formed and may have provided the principle selective force driving E4-mediated inhibition of DSBR.

E4 Products May Prevent Apoptosis

It has recently been shown that DNA PK is required for activation of p53 DNA binding activity by DNA damage induced by ionizing radiation (Woo et al., 1998). This suggests an additional function for the interaction of E4 and DNA PK: by interfering with DNA PK function, E4 products may prevent activation of p53, and thus apoptosis, induced by the DNA damage signaling pathway in response to viral DNA replication. Adenovirus DNA replication produces large quantities of linear, double-stranded viral DNA and partially single-stranded replication intermediates (Lechner and Kelly, 1977). These molecules are likely to be perceived by the DNA damage sensing system as the products of massive cellular DNA damage and therefore are likely to induce rapid apoptosis. In the context of an adenovirus infection, interference with DNA PK-dependent transduction of DNA damage signals therefore may be anti-apoptotic. Prevention of early apoptotic cell death contributes to the efficiency of viral infections (Hardwick, 1998) and a mechanism that interferes specifically with apoptosis induced by the products of viral DNA replication, like other viral anti-apoptotic measures, may provide a valuable survival advantage. The DNA PK-related ATM protein kinase also participates in transduction of DNA damage signals to p53 (Canman et al., 1998, Banin et al., 1998), and complete protection of infected cells from apoptosis induced by the DNA damage sensing system may require inhibition of ATM activity as well as that of DNA PK. The amino acid sequence homology between DNA PK and ATM makes it plausible that E4 products will prove to bind to and regulate ATM as they may DNA PK.

Other viruses might require protection from genome concatenation by DSBR or from apoptosis induced by the structure of their genomes or replication intermediates, suggesting that inhibition of DNA PK-dependent signal transduction will be widespread in viral life cycles. It is interesting that the herpesvirus Vmw110 (ICP0) protein attenuates DNA PK activity by inducing degradation of DNA $PK_{cs}$ (Lees-Miller et al., 1996). Vmw110 mutants are viable; however, their yield is higher in MO59J (DNA PK⁻) than in MO59K (DNA PK⁺) cells, confirming the biological relevance of the reduction in DNA PK activity (Parkinson, Lees-Miller, and Everett, 1999).

The studies described here indicate that adenovirus E4 encodes products that overcome a newly-recognized block to viral infection, genome concatenation, by a novel mechanism, inhibition of DSBR. The data also suggest that by ablating an upstream step in the DNA-damage signaling pathway, E4 prevents apoptosis that would otherwise be induced by viral DNA replication. The interactions described here between E4 products and DNA PK are the first instances of interference with the function of a proximal transducer of DNA damage by an oncoprotein (Dobner et al., 1996, Moore, Horikoshi, and Shenk, 1996). Failure to respond appropriately to DNA damage contributes the predisposition to cancer in individuals lacking ATM (Canman et al., 1998, Banin et al., 1998), and ablation of DNA PK activity is likely to have similar consequences. Therefore, the interaction of E4 34k with DNA PK may provide the prototype for a new mechanism by which viral and cellular oncogene products contribute to oncogenesis.

Materials and Methods

Coimmunoprecipitation and Immunoblotting $6.5 \times 10^5$ 293 cells were transfected using LipofectAmine (Life Technologies, Rockville, Md.) with 1.0 mg E4 or empty vector plasmid and 1.0 mg each plasmids expressing B-galactosidase and SV40 large T antigen. The E4 34k expression plasmid OE6.5 is a derivative of pmycRK5 (gift of Dr. Randy Reed, Johns Hopkins University), which contains the SV40 origin of replication and is amplified in the presence of SV40 T antigen in transfected cells. Inserted genes are expressed as fusions with a c-myc epitope. E4 11k was expressed from pORF3D.4, a derivative of pVR1012 (Vical, Inc., San Diego, Calif.). Transfected cells were harvested in 0.25M Tris, pH 7.8, lysed by sonication, clarified by centrifugation, and mixed with an equal volume of 2×NET-2 (NET-2: 50 mM Tris, pH 7.5; 150 mM NaCl; 0.05% NP-40). Lysates were preadsorbed with 50 µl of a 50% suspension of Sepharose CL4B (Sigma) in NET-2 for 30 m at 4° C. and antibodies were added to the preabsorbed lysates as follows: aDNAPK Ab146 and aE4 34k C-term, 3 ml; aDNAPK$_{cs}$ Ab145, 8.3 ml (5 mg IgG); aDNAPK$_{cs}$ mAb2, 5 ml (1.5 mg IgG); and IgG2a (irrelevant control for mAb-2), 15 ml (1.5 mg IgG). Immune complexes were collected using protein A Sepharose (Sigma) and fractionated by SDS-PAGE. Proteins were transferred to nitrocellulose and probed with aE4 34k C-term or Ab145 diluted 1:1000. Immunoreactive bands were detected using horseradish peroxidase-conjugated secondary antibodies and an enhanced chemilumenescent substrate system (Amersham). DNA PK antibodies 145 and 146 (Connelly et al., 1998) were generously provided by Carl Anderson, Brookhaven National Laboratories. mAb2 was purchased from NeoMarkers (Fremont, Calif.). Antibody against the E4 34k carboxyterminus (Boivin et al., 1999) was a generous gift from Philip Branton (McGill University). Antibody against E4 11k was raised in rabbits by immunization with the carboxyterminal peptide ERVHLIDLHFEVLDNLLEZ (SEQ ID NO:3) conjugated to keyhole limpet hemocyanin.

V(D)J Recombination Assay $1.2 \times 10^6$ 293 cells were transfected (Graham and Eb, 1973) with 3.0 mg JH200 (Hesse et al., 1987), 1.5 mg each Rag1 and Rag2 plasmids (Lin and Desiderio, 1993) or 3.0 mg empty vector control, 1.5 mg E4 or empty vector plasmid, and 0.3 mg RSV-driven SV40 T antigen expression plasmid (Swanson and Desiderio, 1998). 48 hours after transfection, cells were collected by scraping into PBS. One-half the cells were reserved for analysis by immunoblotting. Plasmid DNA was extracted from the remainder using a PERFECTprep plasmid DNA kit (5'→3', Boulder, Colo.) and 1 ml of the recovered DNA was introduced into E. coli by electroporation. Transformed cells were assessed for resistance to carbenicillin (100 mg/ml) or carbenicillin (100 mg/ml) and chloramphenicol (30 mg/ml) by plating on LB plates containing antibiotics.

Pulsed-Field Gel Electrophoresis $2 \times 10^5$ MO59J or MO59K cells were infected with $5 \times 10^6$ pfu (determined on W162 cells (Weinberg and Ketner, 1983)) of Ads or H5dl1011. 52 h after infection the cells were trypsinized, rinsed, and resuspended in 200 µl of PBS containing 125 mM EDTA in a 2 ml microcentrifuge tube. 200 µl of 1.25% low gelling temperature agarose in 125 mM EDTA, 50 mM Tris (pH 7.4), melted and cooled to 50° C., was added to the resuspended cells. Solidified plugs were transferred to tubes containing 1 ml of 1.2% SDS, 0.125 mM EDTA, 1 mg/ml Proteinase K. After overnight incubation at 50° C., the plugs were rinsed three times with 50 mM EDTA over 8 hours. Electrophoresis in 1.2% agarose, 0.5×TBE was performed in a GeneNavigator apparatus (Pharmacia, Uppsala, Sweden) in hexagonal field mode for 10 h at 300V, switching time 15 seconds.

Assay of DNA PK Activity

Hela cells were infected at an MOI of 25 pfu/cell with Ad5 or the E4 deletion mutant H5dl1007, or were mock infected. 24 hours after transfection, the cells were harvested by trypsinization, washed twice, swollen in 2 packed cell volumes of LSB (Lees-Miller and Anderson, 1989) and lysed by one freeze-thaw cycle. Lysates were centrifuged at 10,000×G at 4° C. for 10 minutes. Pellets were resuspended in 3 original packed cell volumes of 500 mM KCl, 10 mM MgCl$_2$, 1 mM DTT, 25 mM Hepes pH 7.5, sonicated for 30 seconds on ice, and centrifuged at 100,000×G at 4° C. for 30 minutes. The ability of supernatants to phosphorylate a p53-derived peptide was determined using the SignaTECT DNA-Dependent Protein Kinase Assay System (Promega, Madison, Wis.), after removal of endogenous DNA from the extracts by DEAE Sepharose chromatography as recommended by Promega. Protein concentrations were determined using the Bio-Rad Protein Assay.

References

Allalunis-Turner, M. J., Barron, G. M., Day, R. S. d., Dobler, K. D., and Mirzayans, R. (1993). Isolation of two cell lines from a human malignant glioma specimen differing in sensitivity to radiation and chemotherapeutic drugs. *Radiat Res* 134, 349–54.

Banin, S., Moyal, L., Shieh, S., Taya, Y., Anderson, C. W., Chessa, L., Smorodinsky, N. I., Prives, C., Reiss, Y., Shiloh, Y., and Ziv, Y. (1998). Enhanced phosphorylation of p53 by ATM in response to DNA damage [In Process Citation]. *Science* 281, 1674–7.

Boivin, D., Morrison, M. R., Marcellus, R. C., Querido, E., and Branton, P. E. (1999). Analysis of synthesis, stability, phosphorylation, and interacting polypeptides of the 34-kilodalton product of open reading frame 6 of the early region 4 protein of human adenovirus type 5 [In Process Citation]. *J Virol* 73, 1245–53.

Bridge, E., and Ketner, G. (1989). Redundant control of adenovirus late gene expression by early region 4. *J Virol* 63, 631–8.

Bridge, E., and Ketner, G. (1990). Interaction of adenoviral E4 and E1b products in late gene expression. *Virology* 174, 345–53.

Canman, C. E., Lim, D. S., Cimprich, K. A., Taya, Y., Tamai, K., Sakaguchi, K., Appella, E., Kastan, M. B., and Siliciano, J. D. (1998). Activation of the ATM kinase by ionizing radiation and phosphorylation of p53 [In Process Citation]. *Science* 281, 1677–9.

Connelly, M. A., Zhang, H., Kieleczawa, J., and Anderson, C. W. (1998). The promoters for human DNA-PKcs (PRKDC) and MCM4: divergently transcribed genes located at chromosome 8 band q11. *Genomics* 47, 71–83.

Dobner, T., Horikoshi, N., Rubenwolf, S., and Shenk, T. (1996). Blockage by adenovirus E4orf6 of transcriptional activation by the p53 tumor suppressor. *Science* 272, 1470–3.

Feinberg, A. P., and Vogelstein, B. (1983). A technique for radiolabeling DNA restriction endonuclease fragments to high specific activity. *Anal Biochem* 132, 6–13.

Graham, F. L., and Eb, A. J. v. d. (1973). A new technique for the assay of infectivity of human adenovirus 5 DNA. *Virology* 52, 456–67.

Graham, F. L., Rudy, J., and Brinkley, P. (1989). Infectious circular DNA of human adenovirus type 5: regeneration of viral DNA termini from molecules lacking terminal sequences. *Embo J* 8, 2077–85.

Hardwick, J. M. (1998). Viral interference with apoptosis. *Semin Cell Dev Biol* 9, 339–49.

Hartley, K. O., Gell, D., Smith, G. C., Zhang, H., Divecha, N., Connelly, M. A., Admon, A., Lees-Miller, S. P., Anderson, C. W., and Jackson, S. P. (1995). DNA-dependent protein kinase catalytic subunit: a relative of phosphatidylinositol 3-kinase and the ataxia telangiectasia gene product. *Cell* 82, 849–56.

Hearing, P., Samulski, R. J., Wishart, W. L., and Shenk, T. (1987). Identification of a repeated sequence element required for efficient encapsidation of the adenovirus type 5 chromosome. *J Virol* 61, 2555–8.

Hesse, J. E., Lieber, M. R., Gellert, M., and Mizuuchi, K. (1987). Extrachromosomal DNA substrates in pre-B cells undergo inversion or deletion at immunoglobulin V-(D)-J joining signals. *Cell* 49, 775–83.

Jeggo, P. A. (1998). DNA breakage and repair. *Adv Genet* 38, 185–218.

Jeggo, P. A., Taccioli, G. E., and Jackson, S. P. (1995). Menage a trois: double strand break repair, V(D)J recombination and DNA-PK. *Bioessays* 17, 949–57.

Lechner, R. L., and Kelly, T. J., Jr. (1977). The structure of replicating adenovirus 2 DNA molecules. *Cell* 12, 1007–20.

Lees-Miller, S. P., and Anderson, C. W. (1989). Two human 90-kDa heat shock proteins are phosphorylated in vivo at conserved serines that are phosphorylated in vitro by casein kinase II. *J Biol Chem* 264, 2431–7.

Lees-Miller, S. P., Godbout, R., Chan, D. W., Weinfeld, M., Day, R. S., 3rd, Barron, G. M., and Allalunis-Turner, J. (1995). Absence of p350 subunit of DNA-activated protein kinase from a radiosensitive human cell line. *Science* 267, 1183–5.

Lees-Miller, S. P., Long, M. C., Kilvert, M. A., Lam, V., Rice, S. A., and Spencer, C. A. (1996). Attenuation of DNA-dependent protein kinase activity and its catalytic subunit by the herpes simplex virus type 1 transactivator ICP0. *J Virol* 70, 7471–7.

Lin, W.-C., and Desiderio, S. (1993). Regulation of V(D)J recombination activator protein RAG-2 by phosphorylation. *Science* 260, 953–59.

McBlane, J. F., van Gent, D. C., Ramsden, D. A., Romeo, C., Cuomo, C. A., Gellert, M., and Oettinger, M. A. (1995). Cleavage at a V(D)J recombination signal requires only RAG1 and RAG2 proteins and occurs in two steps. *Cell* 83, 387–95.

Moore, M., Horikoshi, N., and Shenk, T. (1996). Oncogenic potential of the adenovirus E4orf6 protein. *Proc Natl Acad Sci USA* 93, 11295–301.

Parkinson, J., Lees-Miller, S. P., and Everett, R. D. (1999). Herpes simplex virus type 1 immediate-early protein vmw110 induces the proteasome-dependent degradation of the catalytic subunit of DNA-dependent protein kinase. *J Virol* 73, 650–7.

Rawlins, D. R., Rosenfeld, P. J., Wides, R. J., Challberg, M. D., and Kelly, T. J., Jr. (1984). Structure and function of the adenovirus origin of replication. *Cell* 37, 309–19.

Shin, E. K., Perryman, L. E., and Meek, K. (1997). A kinase-negative mutation of DNA-PK(CS) in equine SCID results in defective coding and signal joint formation. *J Immunol* 158, 3565–9.

Southern, E. M. (1975). Detection of specific sequences among DNA fragments separated by gel electrophoresis. *J Mol Biol* 98, 503–17.

Swanson, P. C., and Desiderio, S. (1998). V(D)J recombination signal recognition: distinct, overlapping DNA-protein contacts in complexes containing RAG1 with and without RAG2. *Immunity* 9, 115–25.

Van der Ploeg, L. H., Schwartz, D. C., Cantor, C. R., and Borst, P. (1984). Antigenic variation in Trypanosoma brucei analyzed by electrophoretic separation of chromosome-sized DNA molecules. *Cell* 37, 77–84.

Weiden, M. D., and Ginsberg, H. S. (1994). Deletion of the E4 region of the genome produces adenovirus DNA concatemers. *Proc Natl Acad Sci USA* 91, 153–7.

Weinberg, D. H., and Ketner, G. (1983). A cell line that supports the growth of a defective early region 4 deletion mutant of human adenovirus type 2. *Proc Natl Acad Sci USA* 80, 5383–6.

Woo, R. A., McLure, K. G., Lees-Miller, S. P., Rancourt, D. E., and Lee, P. W. (1998). DNA-dependent protein kinase acts upstream of p53 in response to DNA damage. *Nature* 394, 700–4.

What is claimed is:

1. A method of inhibiting repair of double-stranded breaks in DNA in a cell which comprises introducing into the cell DNA comprising early region 4 (E4) open reading frame 6 (ORF6) and an E1B region of genomic adenoviral DNA, wherein only the gene products of said early region 4 (E4) open reading frame 6 (ORF6) and said E1B region of genomic adenoviral DNA are expressed in said cell in a quantity sufficient to inhibit repair of double-stranded breaks in DNA in said cell.

2. The method of claim 1 wherein said step of introducing is performed by transfection.

3. The method of claim 1, wherein said E1B region of genomic adenoviral DNA encodes and expresses only E1B 55 kDa protein.

4. The method of claim 1, wherein said gene products of said E1B region include only the E1B 55 kDa protein.

* * * * *